(12) United States Patent
Nakayama et al.

(10) Patent No.: US 11,497,387 B2
(45) Date of Patent: Nov. 15, 2022

(54) JOINT MECHANISM, MANIPULATOR, AND MANIPULATOR SYSTEM

(71) Applicant: OLYMPUS CORPORATION, Tokyo (JP)

(72) Inventors: Shingo Nakayama, Tokyo (JP); Kosuke Kishi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 790 days.

(21) Appl. No.: 16/456,320

(22) Filed: Jun. 28, 2019

(65) Prior Publication Data

US 2019/0313882 A1 Oct. 17, 2019

Related U.S. Application Data

(60) Division of application No. 15/205,591, filed on Jul. 8, 2016, now abandoned, which is a continuation of
(Continued)

(30) Foreign Application Priority Data

Jan. 14, 2014 (JP) .................................. 2014-004376

(51) Int. Cl.
*A61B 34/00* (2016.01)
*A61B 1/008* (2006.01)
(Continued)

(52) U.S. Cl.
CPC ............ *A61B 1/008* (2013.01); *A61B 1/0055* (2013.01); *A61B 1/0057* (2013.01); *A61B 34/71* (2016.02);
(Continued)

(58) Field of Classification Search
CPC ...... A61B 1/008; A61B 1/0055; A61B 1/0057
See application file for complete search history.

(56) References Cited

U.S. PATENT DOCUMENTS 8,182,418 B2 * 5/2012 Durant ................. A61B 1/0055
600/141
2003/0018323 A1 1/2003 Wallace et al.
(Continued)

FOREIGN PATENT DOCUMENTS

EP  2 735 278 A2  5/2014
EP  3 087 901 A1  11/2016
(Continued)

OTHER PUBLICATIONS

Extended Supplementary European Search Report dated Oct. 5, 2017 in European Patent Application No. 15 73 7635.1.
(Continued)

*Primary Examiner* — Eyamindae C Jallow
(74) *Attorney, Agent, or Firm* — Scully, Scott, Murphy & Presser, P.C.

(57) ABSTRACT

A manipulator including joint mechanisms each including: first and second members extending along a central axis; the second member disposed at a distal end of the first member and being swivelable relative to the first member about a swivel axis; a guide sheath extending near the central axis, a distal end of the guide sheath being fixed to the second member; a manipulation wire introduced toward the distal end of the guide sheath; and a pulley provided in the second member such that the manipulation wire is wound at least partially around the pulley to cause a distal end of the wire to change direction towards the first member, the pulley being rotatable about an axis parallel to the swivel axis; wherein the distal end of the manipulation wire is fixed to the first member near the inner surface of the through hole.

17 Claims, 18 Drawing Sheets

Related U.S. Application Data application No. PCT/JP2015/050541, filed on Jan. 9, 2015.

(51) Int. Cl.
*A61B 1/005* (2006.01)
*A61B 17/00* (2006.01)

(52) U.S. Cl.
CPC .............. *A61B 2017/00314* (2013.01); *A61B 2017/00323* (2013.01)

(56) References Cited

U.S. PATENT DOCUMENTS

| | | |
|---|---|---|
| 2004/0054322 A1 | 3/2004 | Vargas |
| 2004/0242966 A1* | 12/2004 | Barry .................. A61B 1/0057 600/146 |
| 2006/0178556 A1 | 8/2006 | Hasser et al. |
| 2007/0035143 A1 | 2/2007 | Blackwell et al. |
| 2008/0221592 A1 | 9/2008 | Kawai |
| 2009/0099420 A1* | 4/2009 | Woodley ............ A61B 1/0053 600/142 |
| 2009/0216083 A1* | 8/2009 | Durant ................ A61B 1/0055 600/130 |
| 2009/0326325 A1 | 12/2009 | Naito et al. |
| 2010/0241135 A1 | 9/2010 | Iida et al. |
| 2012/0190920 A1 | 7/2012 | Aho et al. |
| 2013/0090598 A1 | 4/2013 | Vargas |
| 2013/0255410 A1* | 10/2013 | Lee .................... A61B 1/0055 74/89.22 |
| 2014/0228642 A1 | 8/2014 | Vargas |
| 2014/0288568 A1 | 9/2014 | Vargas |
| 2014/0296779 A1 | 10/2014 | Vargas |
| 2015/0313452 A1 | 11/2015 | Hasser et al. |

FOREIGN PATENT DOCUMENTS

| | | |
|---|---|---|
| JP | H05-185385 A | 7/1993 |
| JP | 2004-223687 A | 8/2004 |
| JP | 2004-223688 A | 8/2004 |
| JP | 2007-29290 A | 2/2007 |
| JP | 2007-175502 A | 7/2007 |
| JP | 2009-539573 A | 11/2009 |
| JP | 2010-220684 A | 10/2010 |
| JP | 2010-259479 A | 11/2010 |
| JP | 2012-152562 A | 8/2012 |
| JP | 2012-196269 A | 10/2012 |
| JP | 2013-046772 A | 3/2013 |
| JP | 5197980 B2 | 5/2013 |
| WO | 2007/120353 A2 | 10/2007 |
| WO | 2007/146987 A2 | 12/2007 |

OTHER PUBLICATIONS

International Search Report dated Apr. 7, 2015 issued in PCT/JP2015/050541.
Office Action dated Feb. 28, 2019 received in U.S. Appl. No. 15/205,591.
Office Action dated Nov. 15, 2018 received in U.S. Appl. No. 15/205,591.

* cited by examiner

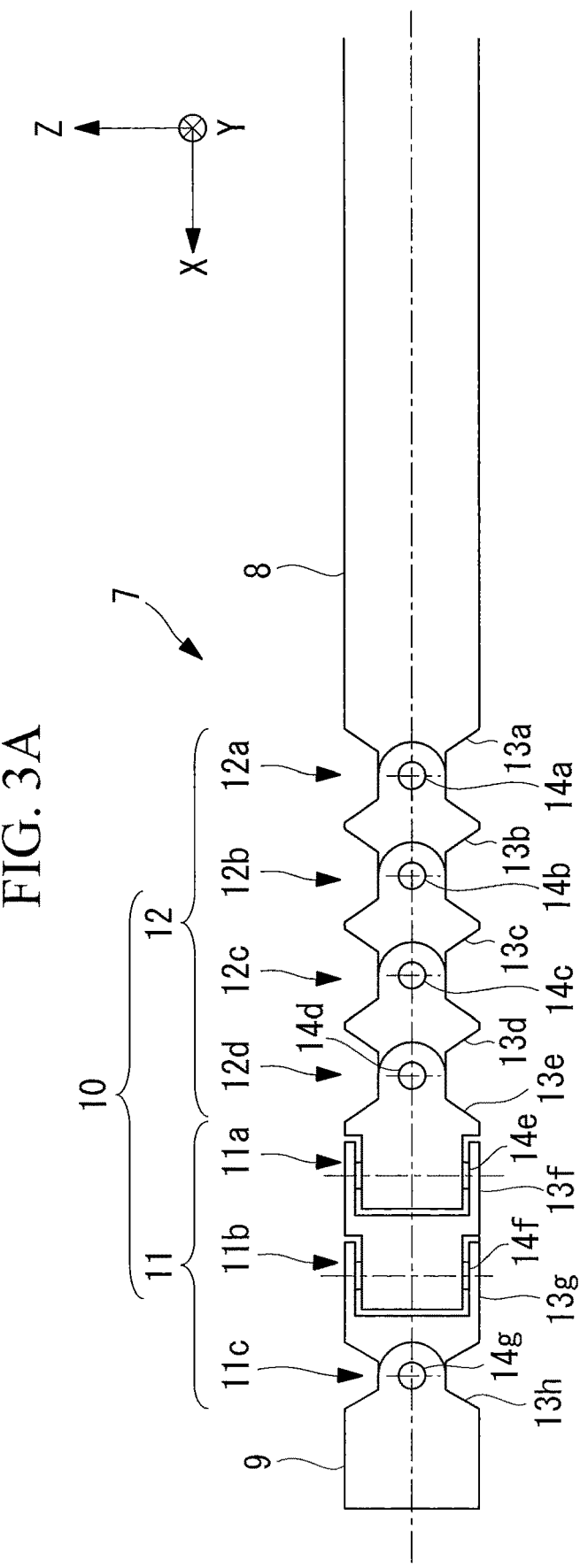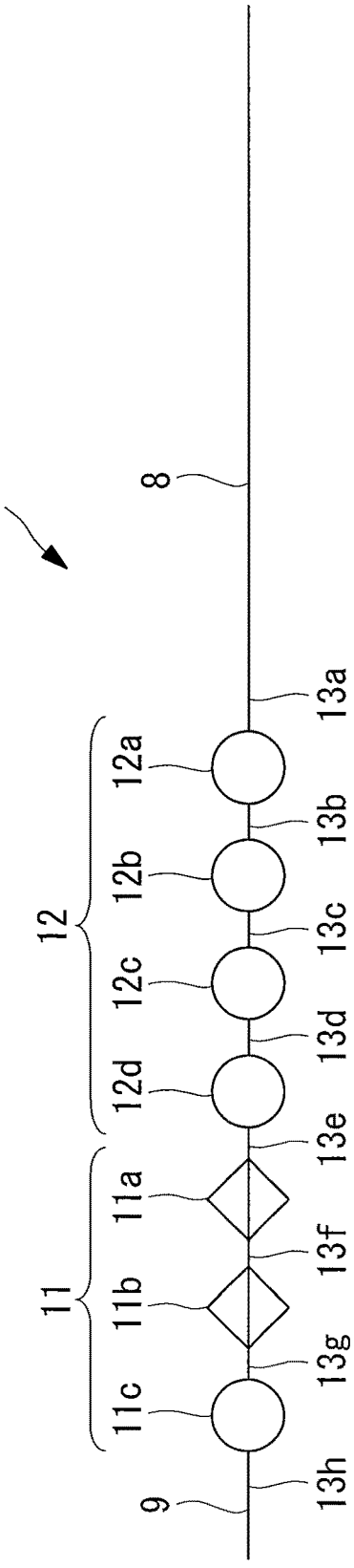

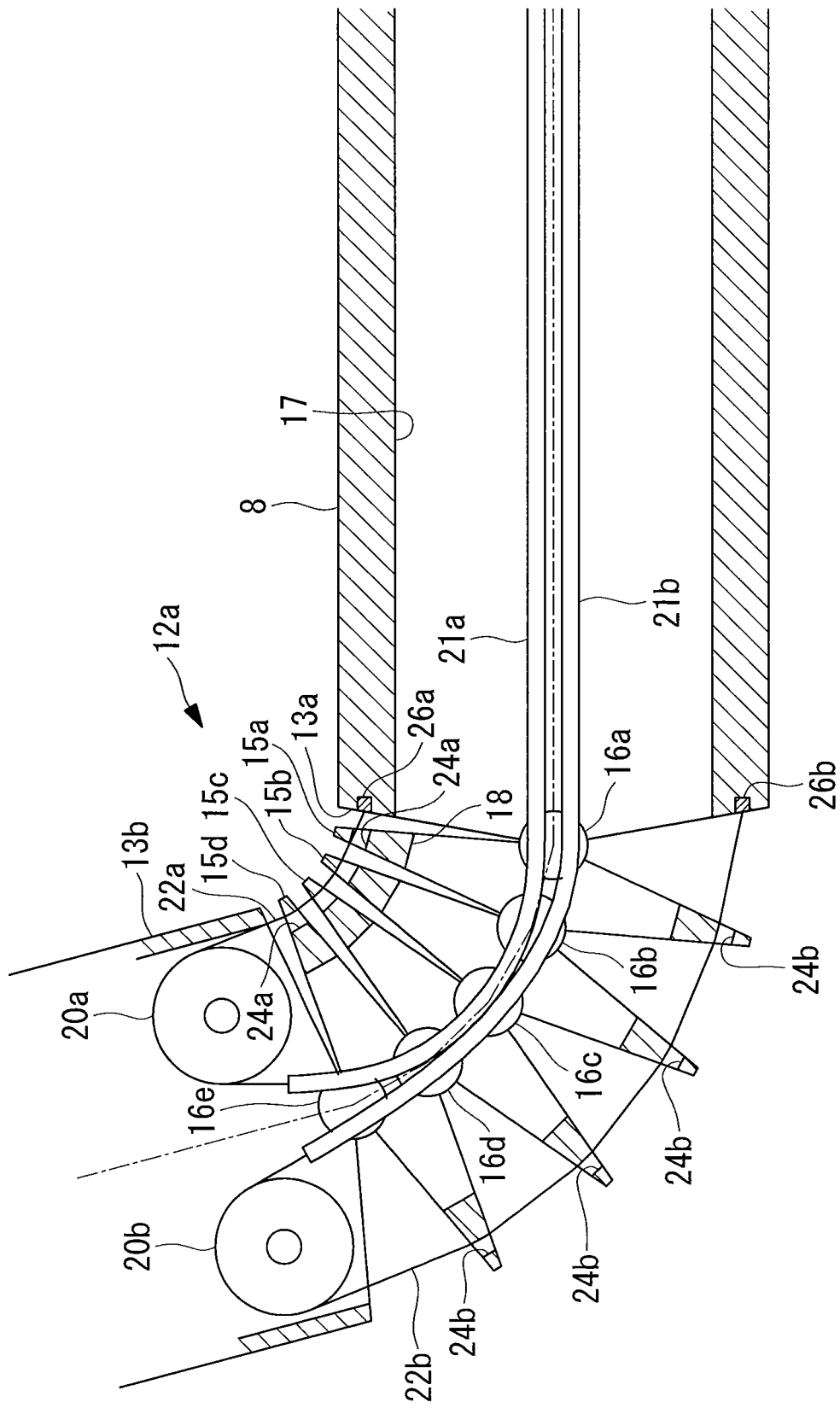

JOINT MECHANISM, MANIPULATOR, AND MANIPULATOR SYSTEM

CROSS REFERENCE TO RELATED APPLICATIONS

This application is a divisional application of U.S. application Ser. No. 15/205,591, filed on Jul. 8, 2016, which is a continuation of International Application PCT/JP2015/050541, with an international filing date of Jan. 9, 2015, which is hereby incorporated by reference herein in its entirety. This application claims the benefit of Japanese Patent Application No. 2014-004376, the content of which is incorporated herein by reference.

TECHNICAL FIELD

The present invention relates to joint mechanisms, manipulators, and manipulator systems.

BACKGROUND ART

In the related art, a known medical device has a multi-joint bending mechanism in which a plurality of bending segments connected in a swivelable manner are independently and individually manipulated by means of manipulation wires (for example, see Patent Literature 1).

In this multi-joint bending mechanism, a position close to the outer periphery of each bending segment is pulled toward the basal end by using each manipulation wire so as to generate moment. Therefore, in order to efficiently transmit a traction force to the bending segments, the manipulation wires and tubular guide sheaths that guide the manipulation wires are routed so as to extend along paths located relatively close to the outer peripheries of the bending segments.

Furthermore, in the multi-joint bending mechanism in Patent Literature 1, the manipulation wire connected to the bending segments located closer toward the basal end is disposed at the inner side, in the radial direction of the bending segments, relative to the manipulation wire connected to the bending segments located closer toward the distal end. By applying a traction force to the manipulation wires, each bending segment swivels relative to the other bending segments, thus causing the manipulation wires and the guide sheaths to bend.

CITATION LIST

Patent Literature

{PTL 1}
The Publication of Japanese Patent No. 5197980

SUMMARY OF INVENTION

Technical Problem

The present invention provides a joint mechanism, a manipulator, and a manipulator system that can achieve bendability with a small traction force, reduced device size, and improved controllability.

Solution to Problem

A first aspect of the present invention provides a joint mechanism including a tubular first member having a through-hole extending along a central axis; a second member disposed at a distal end of the first member and swivelable relative to the first member about a swivel axis intersecting the central axis; a flexible, tubular guide sheath extending near the central axis of the through-hole in the first member and a distal end of which is fixed to the second member; a manipulation wire introduced toward the distal end of the guide sheath via the guide sheath; and a turnaround section that is provided in the second member at a position decentered from the swivel axis in a radial direction and that causes the manipulation wire introduced from the first member via the guide sheath to make a U-turn toward the first member. A distal end of the manipulation wire caused to make a U-turn at the turnaround section is fixed to the first member at a position decentered from the swivel axis in the radial direction.

A second aspect of the present invention provides a manipulator including two or more series-connected joint mechanisms described above.

A third aspect of the present invention provides a manipulator including a tubular manipulator body, a basal-end joint unit provided at a distal end of the manipulator body, and a distal-end joint unit connected in series to a distal end of the basal-end joint unit and equipped with at least one joint mechanism described above. The basal-end joint unit includes a swivel member connected to the manipulator body in a swivelable manner about a swivel axis, a tubular guide sheath whose opening at a distal end thereof is fixed to the manipulator body, and a manipulation wire that is introduced via the guide sheath and protrudes from the opening at the distal end of the guide sheath and a distal end of which is fixed to a position decentered from the swivel axis of the swivel member in a radial direction.

A fourth aspect of the present invention provides a manipulator including a tubular manipulator body having a through-hole extending along a central axis; a swivel member disposed at a distal end of the manipulator body and swivelable relative to the manipulator body about a swivel axis intersecting the central axis; a flexible, tubular guide sheath extending near the central axis of the through-hole in the manipulator body and a distal end of which is fixed to the swivel member; a manipulation wire introduced toward the distal end of the guide sheath via the guide sheath; and a turnaround section that is provided in the swivel member and that causes the manipulation wire introduced from the manipulator body via the guide sheath to make a U-turn toward the manipulator body. A distal end of the manipulation wire caused to make a U-turn at the turnaround section is fixed to the manipulator body at a position decentered from the swivel axis in the radial direction.

A fifth aspect of the present invention provides a manipulator system including the above-described manipulator, a slave device equipped with a driver that drives the manipulator, a master device equipped with an operation section to be operated by an operator, and a controller that controls the driver of the slave device based on an input signal input via the operation section of the master device.

BRIEF DESCRIPTION OF DRAWINGS

FIG. 3A is a simplified side view of a bendable section of the endoscope in FIG. 2.

FIG. 3B is a schematic side view of a bendable section of the endoscope in FIG. 2.

FIG. 16 is a vertical sectional view illustrating a bendable section having a single flexure joint.

DESCRIPTION OF EMBODIMENTS

A joint mechanism, a manipulator, and a manipulator system according to an embodiment of the present invention will be described below with reference to the drawings.

Figure 1:
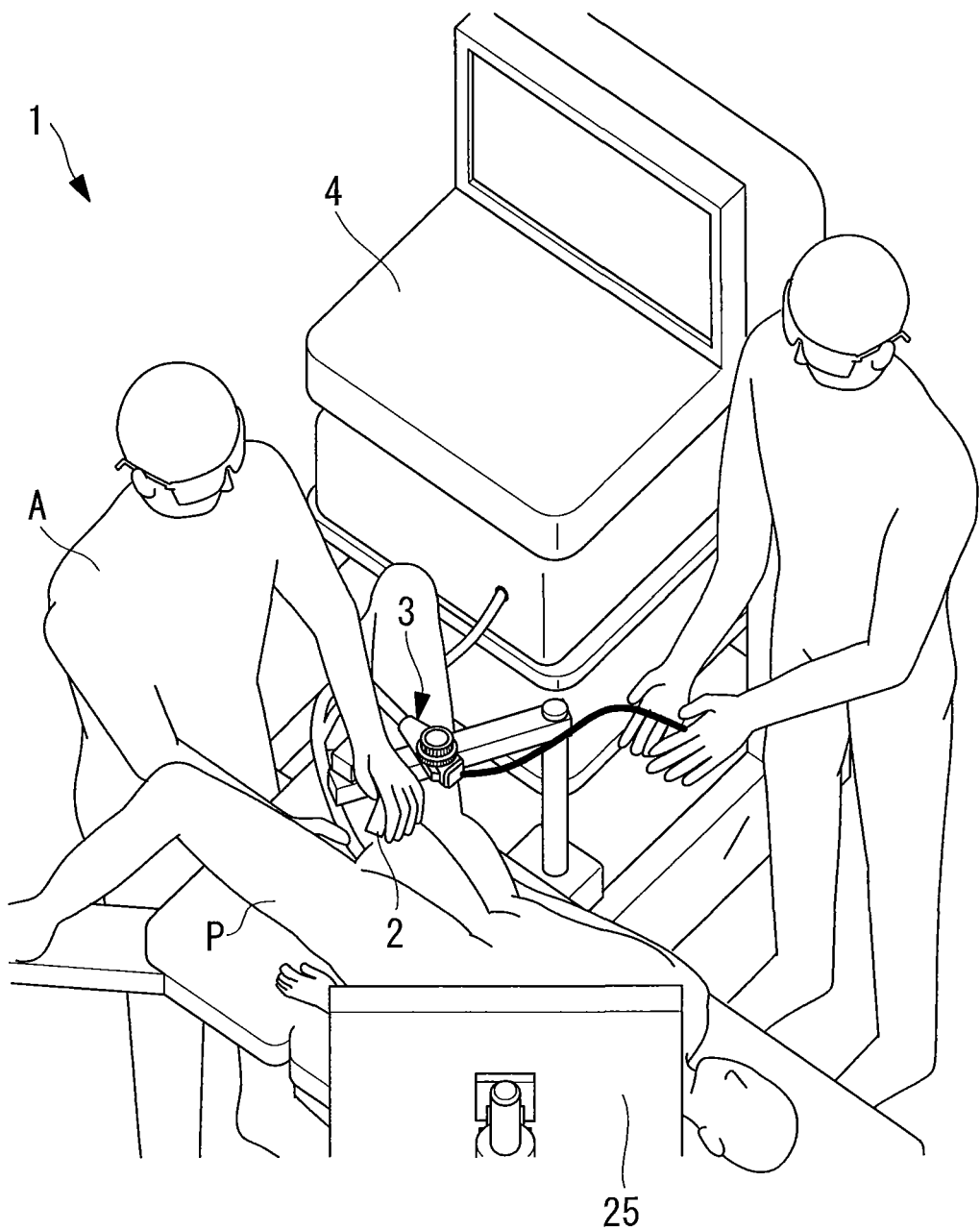
FIG. 1 illustrates the overall configuration of a manipulator system according to an embodiment of the present invention.

As shown in FIG. 1, the manipulator system according to this embodiment is an endoscope system 1 and includes a master device 2 to be operated by a surgeon (operator) A, a slave device 3 driven in accordance with an input via the master device 2, a controller 4 that controls the slave device 3 based on the input to the master device 2, and a monitor 25.

Figure 2:
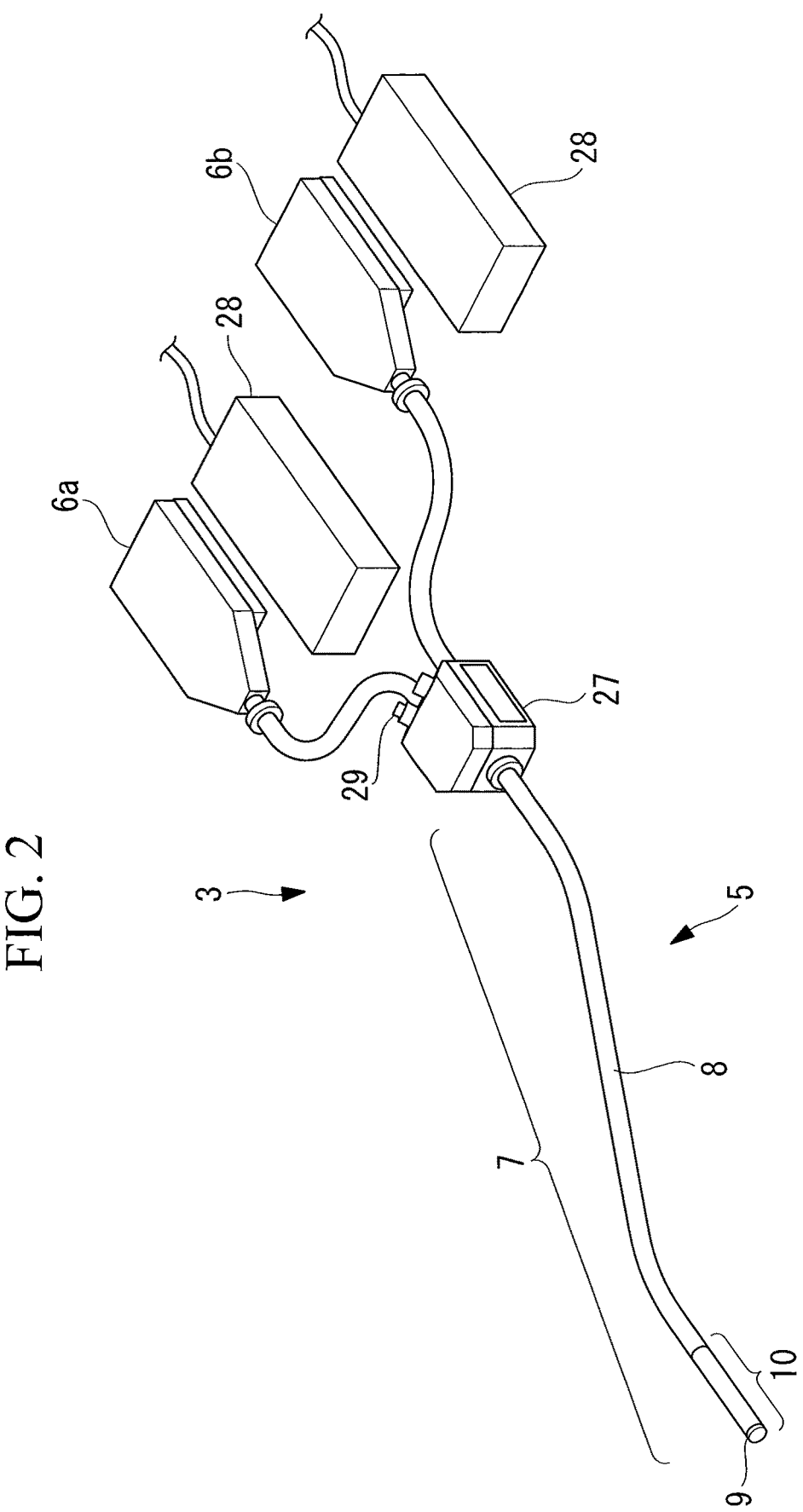
FIG. 2 is a perspective view illustrating a slave device equipped with an endoscope.

As shown in FIG. 2, the slave device 3 includes an endoscope (manipulator) 5 according to this embodiment, which is to be inserted into the body cavity of a patient P, and drivers 6a and 6b that drive the endoscope 5.

The endoscope 5 according to this embodiment is a flexible endoscope having a flexible, elongated insertion part 7, which is bendable, and includes an elongated flexible section (manipulator body) 8, a distal end section 9 disposed at the distal end, and a bendable section 10 disposed between the distal end section 9 and the flexible section 8. Although a flexible endoscope is described in this embodiment, a rigid endoscope having an elongated rigid section may be used as an alternative.

As shown in FIGS. 3A and 3B, the bendable section 10 includes a distal-end joint group 11 and a basal-end joint group 12 for changing the position and the orientation of the distal end section 9 relative to the distal end of the flexible section 8. The distal-end joint group 11 and the basal-end joint group 12 are arranged side-by-side in the longitudinal direction of the insertion part 7. FIG. 3A is a simplified view of the bendable section 10, and FIG. 3B is a schematic view of the bendable section 10.

The basal-end joint group 12 includes a plurality of, for example, four, flexure joints (joint mechanism) 12a to 12d. Each of these flexure joints 12a to 12d is provided between a corresponding pair of link members 13a to 13e and is configured to change the relative angle between the pair of neighboring link members 13a to 13e.

The flexure joints 12a to 12d can be independently flexed about axes 14a to 14d (extending in the Y-axis direction) arranged parallel to one another and spaced apart in the longitudinal direction of the insertion part 7, that is, the longitudinal-axis direction of the link members 13a to 13e. For example, each of the flexure joints 12a to 12d can be flexed in a flexion-angle range of ±60° so that the entire basal-end joint group 12 can be flexed by ±240°. The axes 14a to 14d do not necessarily need to be arranged parallel to one another so long as they are arranged side-by-side to allow for flexion.

The flexure joints 12a to 12d according to this embodiment will be described below with reference to FIGS. 4 to 7.

First, the flexure joint 12a located closest to the basal end will be described in detail.

Figure 4:
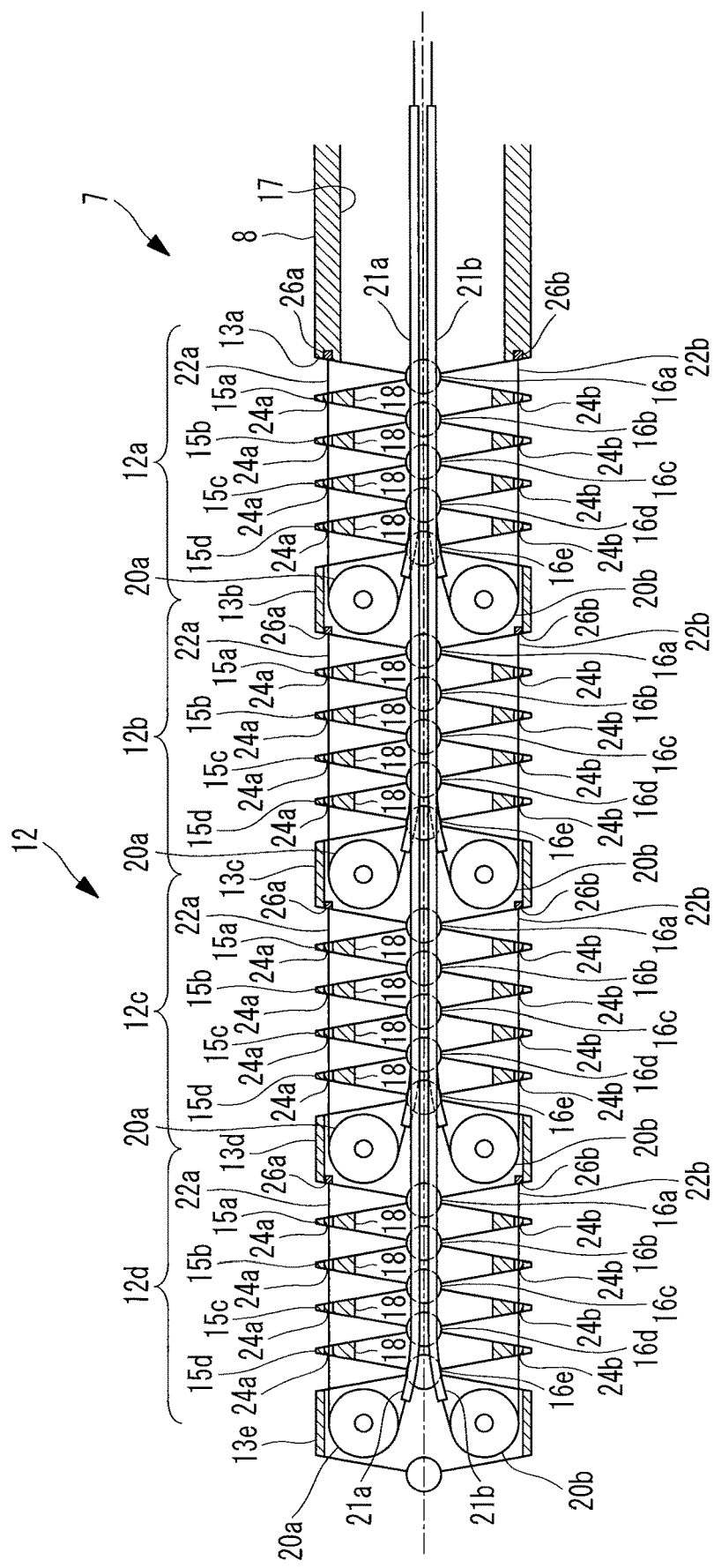
FIG. 4 is a vertical sectional view illustrating a state where a basal-end joint group of the bendable section in FIG. 3A is extending straight.
Figure 5:
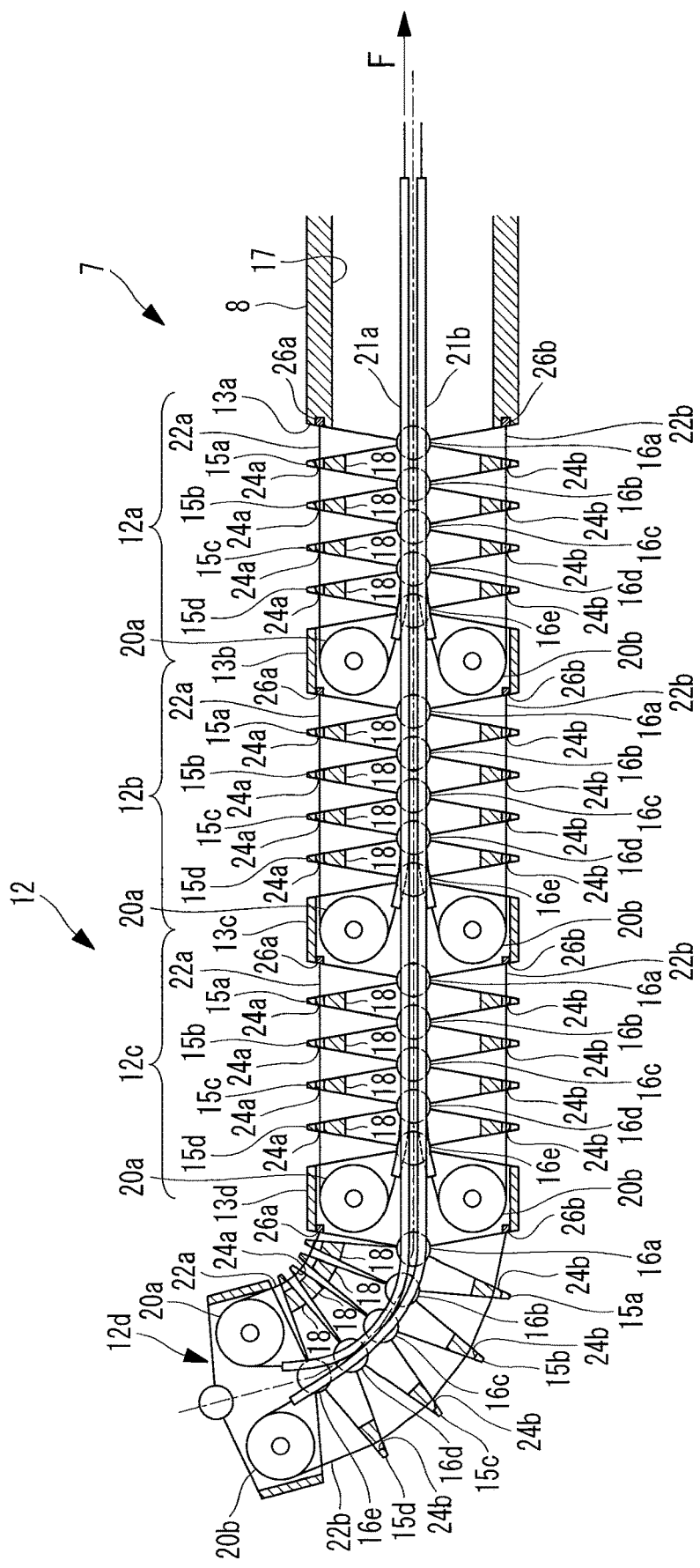
FIG. 5 is a vertical sectional view illustrating a state where a flexure joint at the most distal end of the basal-end joint group of the bendable section in FIG. 3A is flexed.

As shown in FIGS. 4 and 5, the flexure joint 12a includes a link member (first member) 13a serving as an end of the flexible section 8, a link member (second member) 13b, and a plurality of, for example, four, segments (intermediate members) 15a to 15d connected between these link members.

The link members 13a to 13e and the segments 15a to 15d are connected in a relatively swivelable manner about substantially parallel axes (intermediate axes) 16a to 16e. The axes 16a to 16e also do not necessarily need to be disposed parallel to one another so long as they are arranged side-by-side to allow for flexion.

Figure 6:
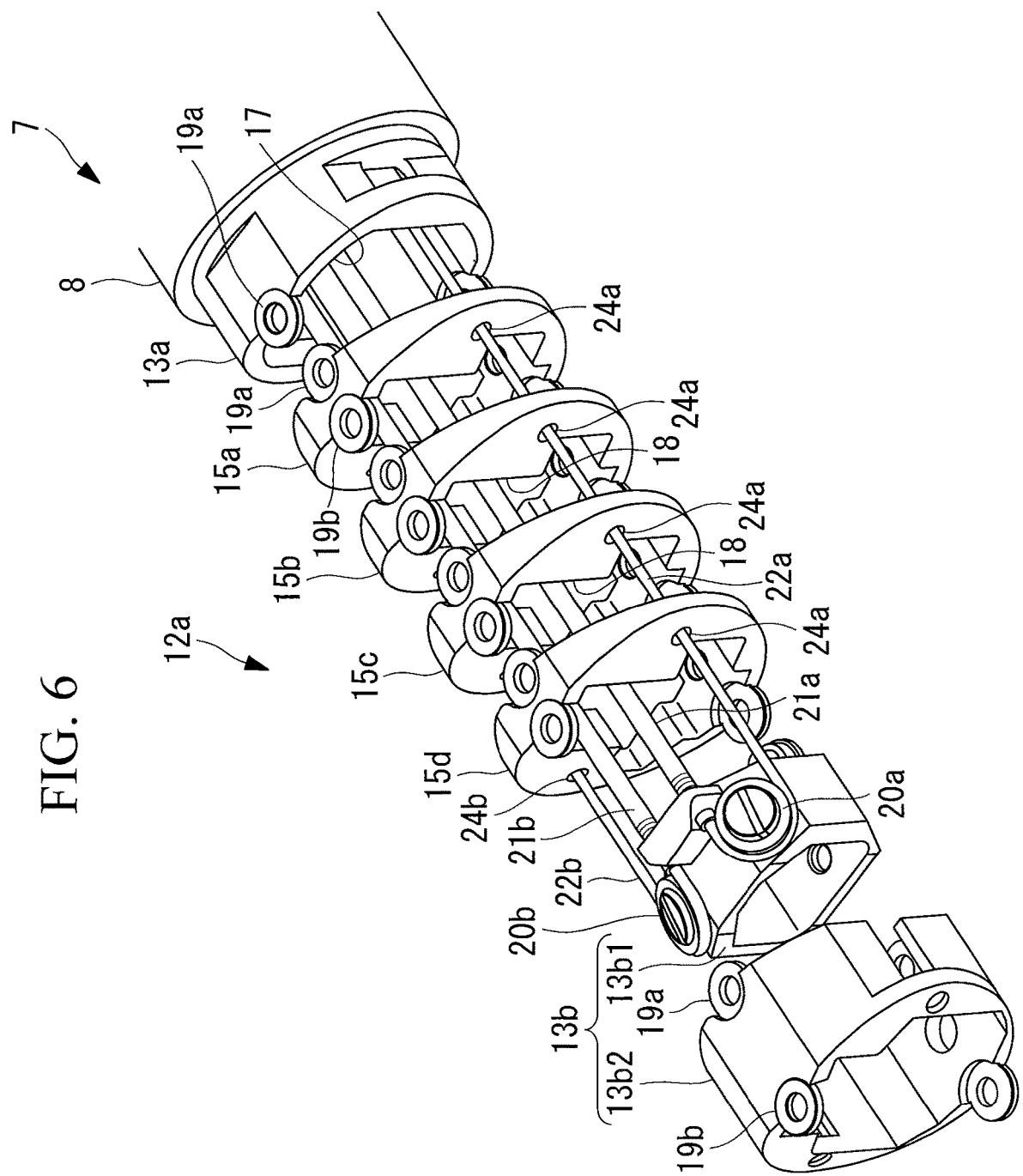
FIG. 6 is an exploded perspective view illustrating a flexure joint at the most basal end of the basal-end joint group of the bendable section in FIG. 3A.

As shown in FIG. 6, the flexible section 8 and the link members 13a and 13b are provided with through-holes 17 extending in the longitudinal direction. The segments 15a to 15d are each formed in the shape of a ring having a through-hole 18 extending in the thickness direction through the middle thereof. The link member 13b and the segments 15a to 15d are each provided with two pairs of connection sections 19a and 19b for connecting it to the link member 13a or 13b or other segments 15a to 15d disposed on the opposite sides thereof in a relatively swivelable manner about two of the substantially parallel axes 16a to 16e. The link member 13b is constituted of a combination of two components 13b1 and 13b2.

The flexure joint 12a according to this embodiment includes two pulleys 20a and 20b rotatably attached to the link member 13b; flexible, tubular guide sheaths 21a and 21b that extend through the through-hole 17 in the flexible section 8 and the through-holes 18 in the segments 15a to 15d, that are disposed along the vicinity of the central axes of the through holes, and whose openings at the distal ends are fixed to the component 13b1 of the link member 13b; and manipulation wires 22a and 22b inserted through the guide sheaths 21a and 21b from the basal end of the flexible section 8.

Figure 7:
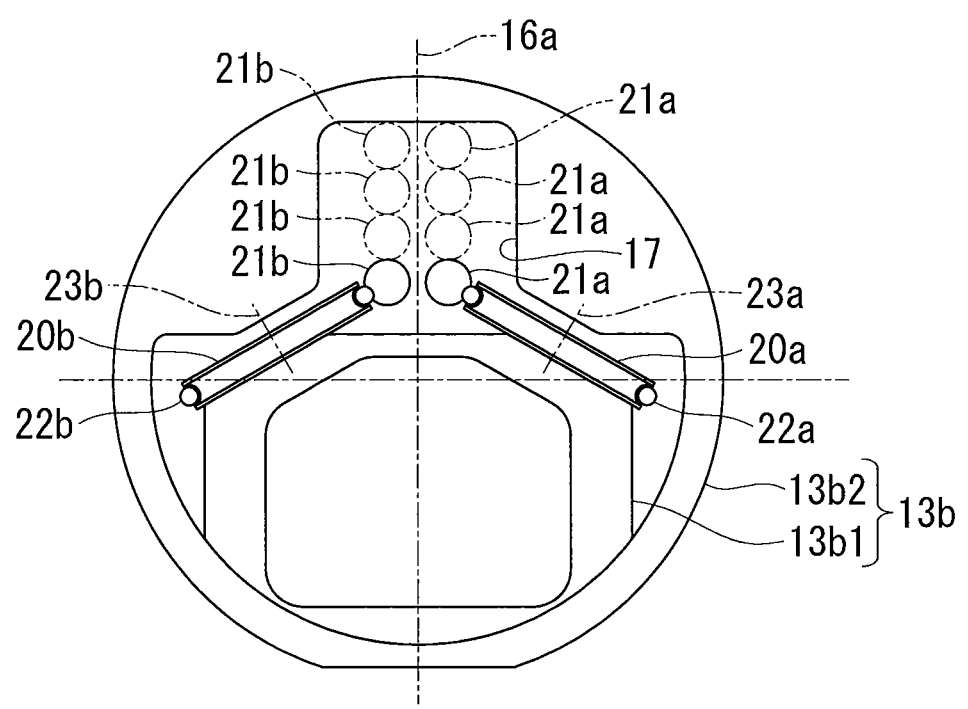
FIG. 7 is a front view of a link member as viewed along a central axis, illustrating the positions of pulleys, guide sheaths, and manipulation wires in the flexure joint in FIG. 5.

As shown in FIG. 7, the pulleys 20a and 20b are attached to the link member 13b at the opposite sides of the axis 16a, which connects the link member 13b and the segment 15a, in a rotatable manner about axes 23a and 23b substantially parallel to the axis 16a. Thus, the pair of pulleys 20a and 20b cause the pair of manipulation wires 22a and 22b protruding from the openings at the distal ends of the pair of guide sheaths 21a and 21b disposed near the axis 16a of the link member 13b to make a U-turn in the reverse direction, thus causing the manipulation wires 22a and 22b to return toward the link member 13a along respective paths near the outer peripheries of the link member 13b and the segments 15a to 15d, which are the most distant from the axis 16a in the radial direction.

Each of the segments 15a to 15d is provided with a pair of through-holes 24a and 24b through which the pair of manipulation wires 22a and 22b, which have been caused to make a U-turn toward the outer periphery by the pair of pulleys 20a and 20b, extend. After the pair of manipulation wires 22a and 22b are turned back in the reverse direction by the pair of pulleys 20a and 20b and extend through the through-holes 24a and 24b in the segments 15a to 15d, the ends thereof are respectively fixed to fixation sections 26a and 26b of the link member 13a.

Figure 8:
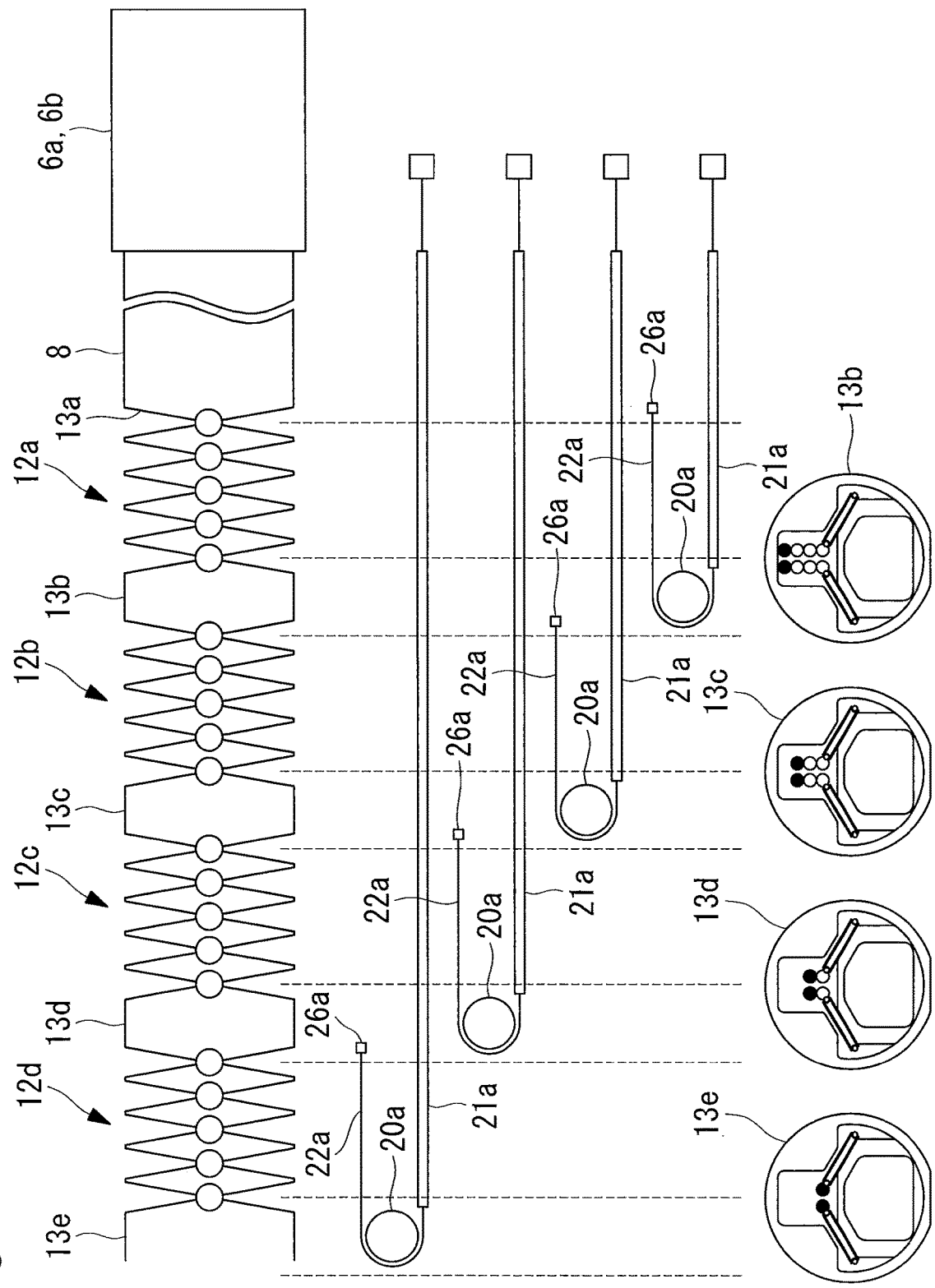
FIG. 8 includes a schematic side view and a front view of each link member, illustrating the positions of the pulleys, the guide sheaths, and the manipulation wires in the basal-end joint group in FIG. 4.

The other flexure joints 12b to 12d have structures identical to that of the flexure joint 12a described above. Specifically, each of the flexure joints 12b to 12d includes four segments 15a to 15d between a first member, which is defined by one of the link members 13b to 13d at the distal end of the remaining one of the flexure joints 12b to 12d adjacent thereto at the basal end, and a second member, which is defined by one of the link members 13c to 13e adjacent thereto at the distal end. The guide sheaths 21a and 21b, the pulleys 20a and 20b, and the manipulation wires 22a and 22b in the flexure joints 12a to 12d are disposed as shown in a simplified view in FIG. 8.

FIG. 5 illustrates the movement of the flexure joint 12d, which is located closest to the distal end, in the basal-end joint group 12. The two manipulation wires 22a and 22b that are guided to the link member 13e by the two guide sheaths 21a and 21b extending in the longitudinal direction from the basal end of the insertion part 7 to the link member 13e at the distal end of the flexure joint 12d are caused to make a U-turn by the pulleys 20a and 20b and are fixed to the fixation sections 26a and 26b in the link member 13d at the basal end of the flexure joint 12d. From the state shown in FIG. 4 in which the flexure joints 12a to 12d are all extending straight, a traction force F is applied to the manipulation wire 22a, as shown in FIG. 5, so that the distal-end flexure joint 12d alone can be flexed in one direction. In this case, the manipulation wire 22b is fed by an amount necessary for the flexion.

As shown in FIG. 3A, the distal-end joint group 11 includes a plurality of, for example, three, flexure joints (distal-end flexure joints) 11a to 11c. Each of these flexure joints 11a to 11c is similarly disposed between a corresponding pair of link members 13f to 13h and is configured to change the relative angle between the pair of neighboring link members 13f to 13h.

As shown in FIG. 3A, the two flexure joints 11a and 11b closer toward the basal end are configured to cause the link members 13f to 13h to swivel about axes 14e and 14f (which extend in the Z-axis direction) orthogonal to a plane that includes the axis 14d of the flexure joint 12d at the most distal end of the basal-end joint group 12 and the long axes of the link members 13e to 13h. Furthermore, the flexure joint 11c at the most distal end causes the distal end section 9 to swivel about an axis 14g (which extends in the Y-axis direction) orthogonal to a plane that includes the axes 14e and 14f of the flexure joints 11a and 11b and the long axes of the link members 13e to 13h. The axes 14e and 14f do not necessarily need to be orthogonal to the plane that includes the axis 14d and the long axes and may alternatively intersect the plane to allow for flexion.

The manipulation wires 22a and 22b used for moving all of the flexure joints 11a to 11c and 12a to 12d are introduced to the bendable section 10 from the basal end of the flexible section 8 via the through-hole 17 in the flexible section 8.

As shown in FIG. 2, the drivers 6a and 6b include two drivers, namely, a distal-end driver 6a for driving the distal-end joint group 11 and a basal-end driver 6b for driving the basal-end joint group 12. The drivers 6a and 6b are connected to the flexible section 8 of the endoscope 5 via a relay unit 27.

The drivers 6a and 6b are equipped with sliders (not shown) that are attached to the basal ends of the manipulation wires 22a and 22b, which extend toward the basal end through the interior of the flexible section 8, so as to pull the basal ends of the manipulation wires 22a and 22b and adjust the traction force F to be applied individually to the manipulation wires 22a and 22b. The drivers 6a and 6b are attachable to and detachable from drive sources 28 equipped with electrically-driven actuators or manually-operated masters (not shown) of the manually driven type.

The actuators of the drive sources 28 are, for example, linear actuators, such as linear motors. When the drivers 6a and 6b are attached to the actuators, the actuators engage with the sliders of the drivers 6a and 6b. When the actuators are actuated, the sliders slide so as to apply a traction force F to the manipulation wires 22a and 22b.

When manually-operated masters are attached to the drivers 6a and 6b, operation sections engage with the sliders of the drivers 6a and 6b. The sliders slide in accordance with a force applied by the surgeon A so as to apply a traction force F to the manipulation wires 22a and 22b.

The relay unit 27 is provided with an insertion port 29 for inserting a surgical device into a forceps channel (not shown) having an opening in an end surface thereof and extending in the longitudinal direction of the insertion part 7.

As shown in FIG. 1, the master device 2 is an orthomorphic input device having joints equal in number to the number of joints in the bendable section 10 of the endoscope 5. Each joint is equipped with a detector (not shown), such as an encoder, for detecting the flexion angle of the joint. When the surgeon A holds and moves the distal end, the detectors detect and output flexion-angle signals of the joints of the master device 2.

The controller 4 controls the drivers 6a and 6b so as to make the flexion angles of the joints of the master device 2, indicated by the flexion-angle signals output from the master device 2, equal to the flexion angles of the flexure joints 11a to 11c and 12a to 12d in the bendable section 10 of the endoscope 5.

The operation of the flexure joints 12a to 12d, the endoscope 5, and the endoscope system 1 according to this embodiment having the above-described configuration will be described below.

In order to observe and treat the inside of the body of the patient P by using the endoscope 5 according to this embodiment, a process for inserting the endoscope 5 into the body cavity is performed by attaching a manually-operated master only to the distal-end driver 6a that drives the distal-end joint group 11.

While holding and operating the manually-operated master with his/her left hand, the surgeon A holds the insertion part 7 with his/her right hand and inserts the endoscope 5 into the body cavity based on a method similar to that used for an endoscope in the related art. In this case, an image of the state in the body cavity is captured by actuating the endoscope 5 and is displayed on the monitor 25. The surgeon A operates the manually-operated master while viewing the monitor 25 so as to drive the distal-end joint group 11, and inserts the insertion part 7 into the body cavity until the distal end section 9 of the endoscope 5 is brought close to an affected area.

In this state, a drive source 28 or a manually-operated master is not attached to the basal-end driver 6b that drives the basal-end joint group 12. Thus, the basal-end joint group 12 moves by passively following the movement of the distal-end joint group 11. This prevents the insertion process from being hindered by the basal-end joint group 12.

When the distal end section 9 of the insertion part 7 is disposed close to an affected area, a drive source 28 is attached to the basal-end driver 6b so as to switch from the manually-operated master to the drive source 28. The surgeon A then operates the master device 2.

The endoscope 5 according to this embodiment has four flexure joints 12a to 12d, which serve as the basal-end joint group 12 and can altogether be flexed by ±240°. Therefore, the bendable section 10 can be bent into a U-shape so that the distal-end surface of the endoscope 5 can be oriented toward the rear. Moreover, since there is still room for movement of the flexure joints 12a to 12d even in the state where the bendable section 10 is bent in a U-shape, the distal end section 9 of the insertion part 7 can advance or recede. As a result, this is advantageous in that the distal-end surface of the insertion part 7 can be oriented toward an easily observable or treatable position not only for an affected area located toward the front in the direction in which the endoscope 5 is inserted into the body cavity but also for an affected area located in the opposite direction, such as an affected area behind a fold.

In order to cause the flexure joint 12d according to this embodiment to flex as shown in FIG. 5, a traction force F is applied by the drive source 28 to the manipulation wire 22a, which is to be disposed at the inner side of the flexed joint, of the two manipulation wires 22a and 22b routed toward the basal end of the flexible section 8 via the guide sheaths 21a and 21b, thereby pulling the manipulation wire 22a. On the other hand, the other manipulation wire 22b, which is to be disposed at the outer side of the flexed joint, is fed by an amount according to the path length of the outer side of the flexed joint.

Accordingly, the traction force F transmitted to the distal end of the manipulation wire 22a causes tension to occur in the manipulation wire 22a between the pulley 20a on the link member 13e and the fixation section 26a on the link member 13d. This causes the link members 13d and 13e and the segments 15a to 15d therebetween to relatively swivel, so that the pulley 20a on the link member 13e and the fixation section 26a on the link member 13d are brought closer to each other, whereby the flexure joint 12d is flexed. The flexure joints 12a to 12c can be flexed in a similar manner.

In this case, in the flexure joints 12a to 12d, the guide sheaths 21a and 21b that guide the manipulation wires 22a and 22b from the basal end of the flexible section 8 to the link members 13b to 13e located toward the distal end are disposed along the vicinity of the central axes of the flexure joints 12a to 12d. Therefore, the radii of curvature of the guide sheaths 21a and 21b when the flexure joints 12a to 12d are flexed can be maintained at larger values than in a normal case where the sheaths are disposed at the inner side by being set near the outer peripheries of the joints.

Furthermore, the guide sheaths 21a and 21b are disposed along the vicinity of the central axes of the flexure joints 12a to 12d even in a case where the bending direction is inverted. Thus, the variation in the radii of curvature of the sheaths is reduced, and variations in the resistance force against bending, which is generated due to the rigidity of the sheaths, can be minimized.

The guide sheaths 21a and 21b each have a larger diameter and higher bending rigidity than the manipulation wire 22a disposed at the inner side. This is advantageous in that, by maintaining the radii of curvature during flexion at large values, the traction force F required for flexion can be reduced, and variations in the required traction force F can be minimized.

Furthermore, since the manipulation wires 22a and 22b are turned back by the pulleys 20a and 20b to make a U-turn, the manipulation wires 22a and 22b move smoothly with low friction when a traction force F is applied thereto for flexing the flexure joints 12a to 12d. Thus, the traction force F for causing the flexure joints 12a to 12d to flex can be further reduced.

Moreover, since the distal ends of the manipulation wires 22a and 22b turned back by the pulleys 20a and 20b are fixed to the fixation sections 26a and 26b located far, in the radial direction, from the axes 16e of the link members 13a to 13d serving as the first members, large moment can be generated by the traction force F applied to the manipulation wires 22a and 22b, which is advantageous in that the flexure joints 12a to 12d can be flexed efficiently.

Furthermore, in this embodiment, the link members 13b to 13e have identical pulleys 20a and 20b disposed at identical positions and in identical orientations in the circumferential direction and the radial direction, thereby achieving commonality of the link members 13b to 13e and reducing the number of types of components.

Furthermore, the endoscope 5 according to this embodiment having the above-described flexure joints 12a to 12d can minimize changes in the traction force F in accordance with the degree of flexion of the flexure joints 12a to 12d. This is advantageous in that the controllability using the drivers 6a and 6b can be improved.

Moreover, with the endoscope system 1 according to this embodiment, the controllability of the endoscope 5 is improved so that the responsiveness of the slave device 3 to the operation of the master device 2 is improved, which is advantageous in that improved manipulability can be achieved.

In the flexure joints 12a to 12d according to this embodiment, the pair of guide sheaths 21a and 21b that guide the pair of manipulation wires 22a and 22b for bending the flexure joints 12a to 12d toward both sides are disposed adjacent to each other with the axes 16a to 16e interposed therebetween. Alternatively, if space permits, the pair of guide sheaths 21a and 21b are preferably arranged in a single line on the axes 16a to 16e. Thus, when the flexure joints 12a to 12d are to be flexed toward both sides, all radii of curvature of the guide sheaths 21a and 21b can be made the same so that the path lengths of the sheaths become fixed, thereby eliminating the need to warp the sheaths and minimizing the traction force required for flexion.

Figure 9:
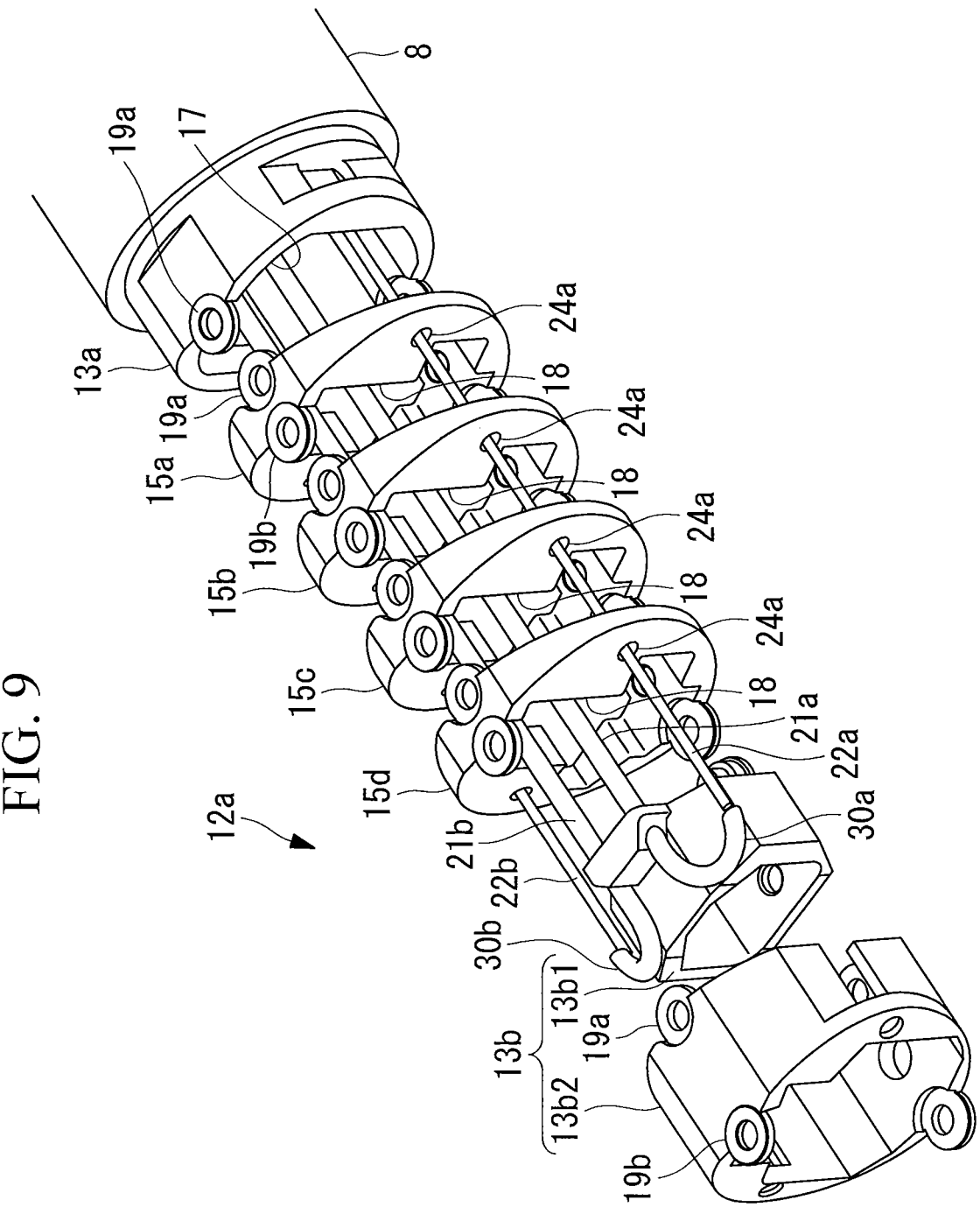
FIG. 9 is an exploded perspective view illustrating a modification of FIG. 6.

Furthermore, although the pulleys 20a and 20b are used as turnaround sections that cause the manipulation wires 22a and 22b to make a U-turn in this embodiment, U-shaped tubular members 30a and 30b that are composed of a high-rigidity material and that allow the manipulation wires 22a and 22b to extend therethrough to make a U-turn may be used as an alternative, as shown in FIG. 9. With this configuration, the manipulation wires 22a and 22b move smoothly through the tubular members 30a and 30b while fixed curvatures are maintained by the tubular members 30a and 30b, so that the bending operation can be performed with a small traction force F. Moreover, with this structure that does not have movable components like the rotating pulleys 20a and 20b, increased durability can be achieved.

Figure 10A:
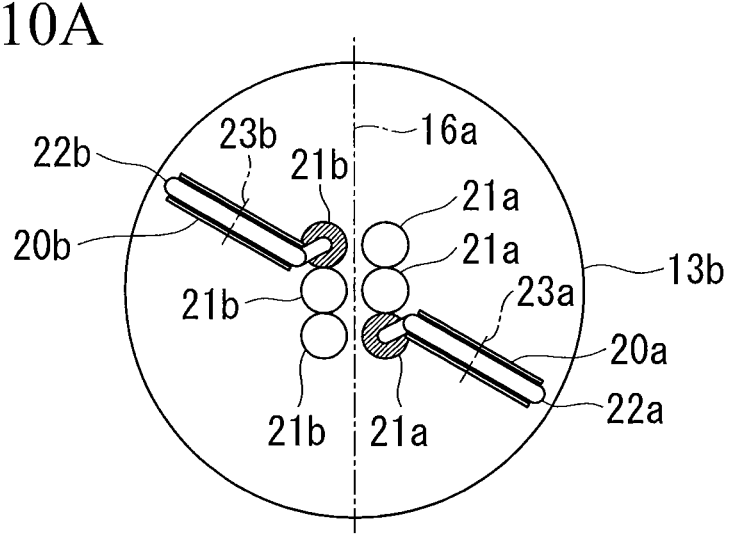
FIG. 10A illustrates a modification of the positions of the pulleys in FIG. 7 and is a front view showing the link member located closest to the basal end.
Figure 10B:
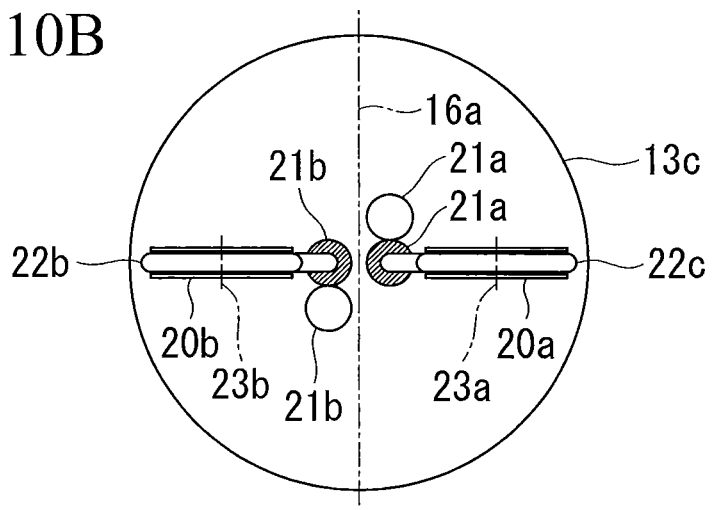
FIG. 10B illustrates a modification of the positions of the pulleys in FIG. 7 and is a front view showing the second link member from the basal end.
Figure 10C:
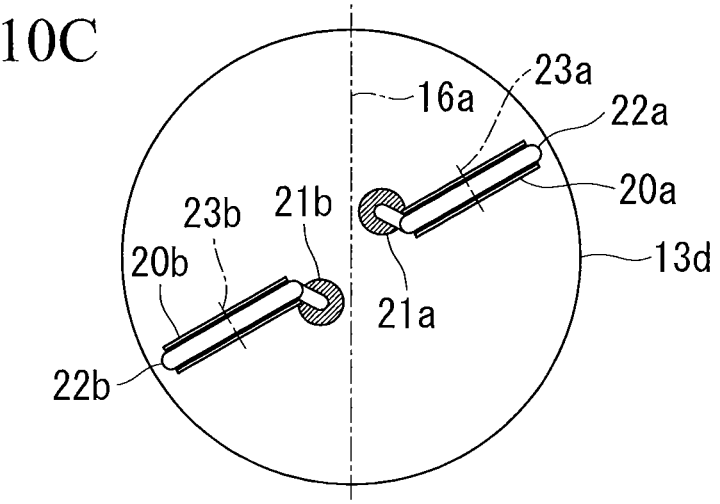
FIG. 10C illustrates a modification of the positions of the pulleys in FIG. 7 and is a front view showing the third link member from the basal end.

Furthermore, in this embodiment, the positions of the pulleys 20a and 20b are identical among all of the link members 13b to 13e serving as the second members. Alternatively, as shown in FIGS. 10A, 10B, and 10C, the positions of the pulleys 20a and 20b may be varied in the circumferential direction among different link members 13b to 13d. The diagonal lines indicate the guide sheaths 21a and 21b that guide the manipulation wires 22a and 22b to the pulleys 20a and 20b of the corresponding link members 13b to 13d. Consequently, the openings at the distal ends of the guide sheaths 21a and 21b can be brought close to the pulleys 20a and 20b, which is advantageous in that the routing of the manipulation wires 22a and 22b from the guide sheaths 21a and 21b can be performed without difficulty.

Figure 11:
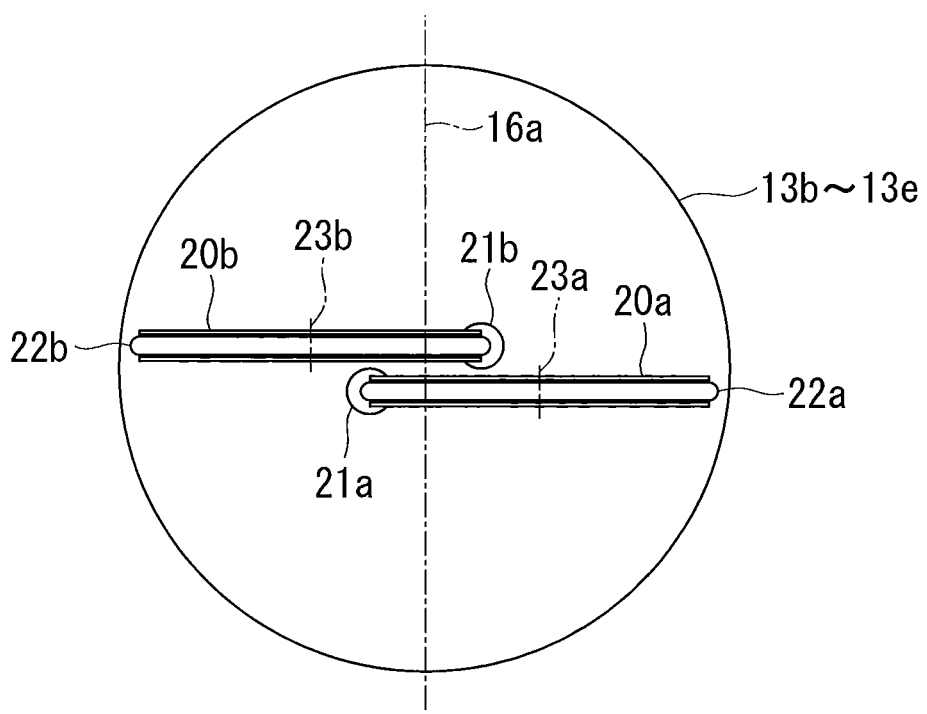
FIG. 11 is a front view illustrating a modification of the pulleys in FIG. 7.

Furthermore, in this embodiment, the pair of pulleys 20a and 20b are disposed at symmetric positions at the opposite sides of the axis 16a. Alternatively, as shown in FIG. 11, the pair of pulleys 20a and 20b may be shifted in the thickness direction so as to partially overlap each other in the radial direction. With this arrangement, large diameters can be ensured for the pulleys 20a and 20b, so that the radii of curvature of the manipulation wires 22a and 22b to be turned back can be increased, thereby reducing the load on the manipulation wires 22a and 22b.

Figure 12:
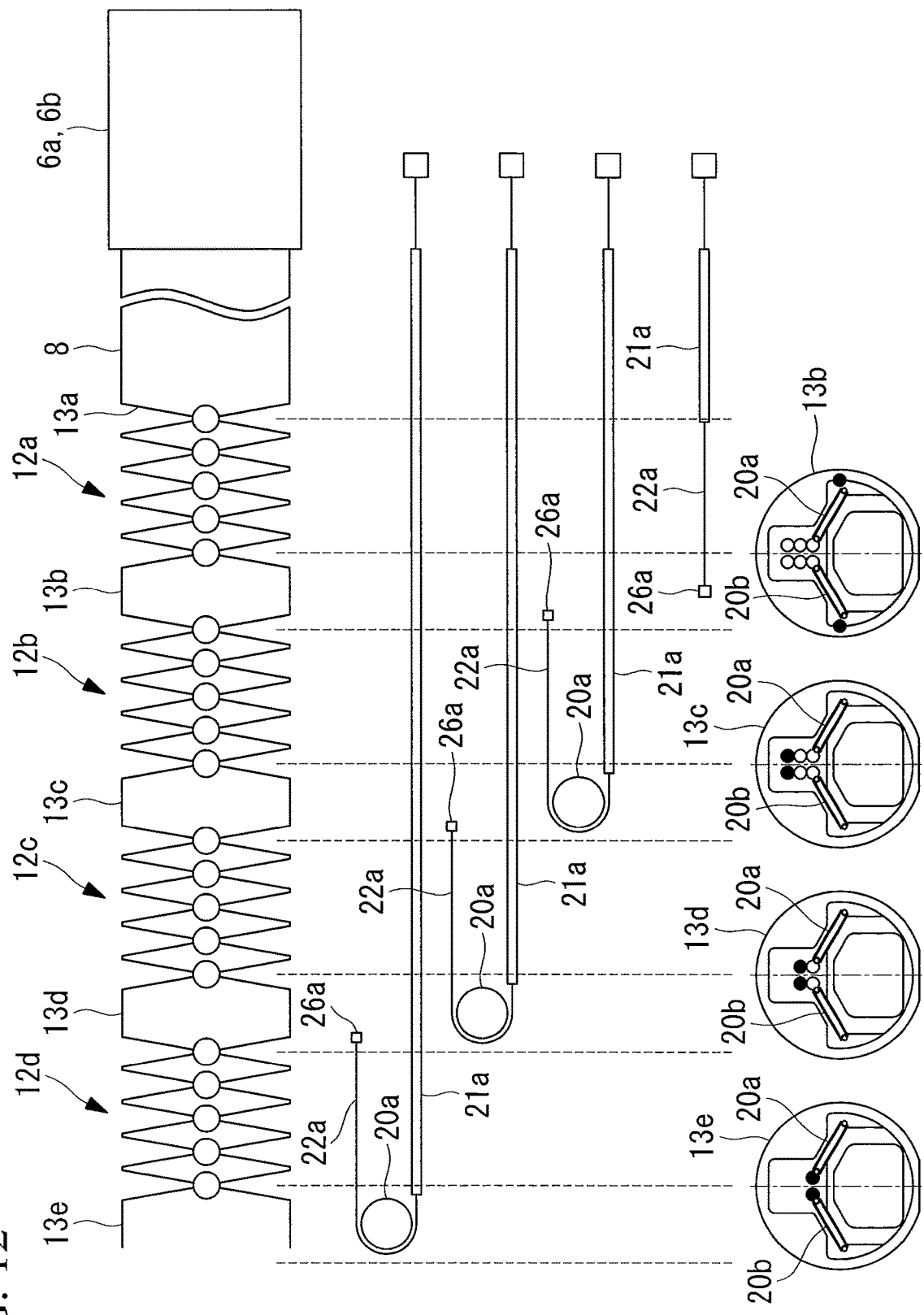
FIG. 12 illustrates a modification of FIG. 8 and includes a schematic side view and a front view of the link members.

Furthermore, in this embodiment, the pulleys 20a and 20b in all of the flexure joints 12a to 12d cause the manipulation wires 22a and 22b to make a U-turn. Alternatively, as shown in FIG. 12, the flexure joint 12a located closest to the distal end may employ a method of pulling the link member 13b toward the basal end by using manipulation wires 22a and 22b extended toward the distal end from the guide sheaths 21a and 21b fixed to the link member 13a at the end of the flexible section 8. With such a configuration, the guide sheaths 21a and 21b can be disposed at positions where they do not bend in accordance with the flexion of the flexure joint 12a, so that the pulleys 20a and 20b can be omitted, thereby achieving a simplified structure.

Figure 13:
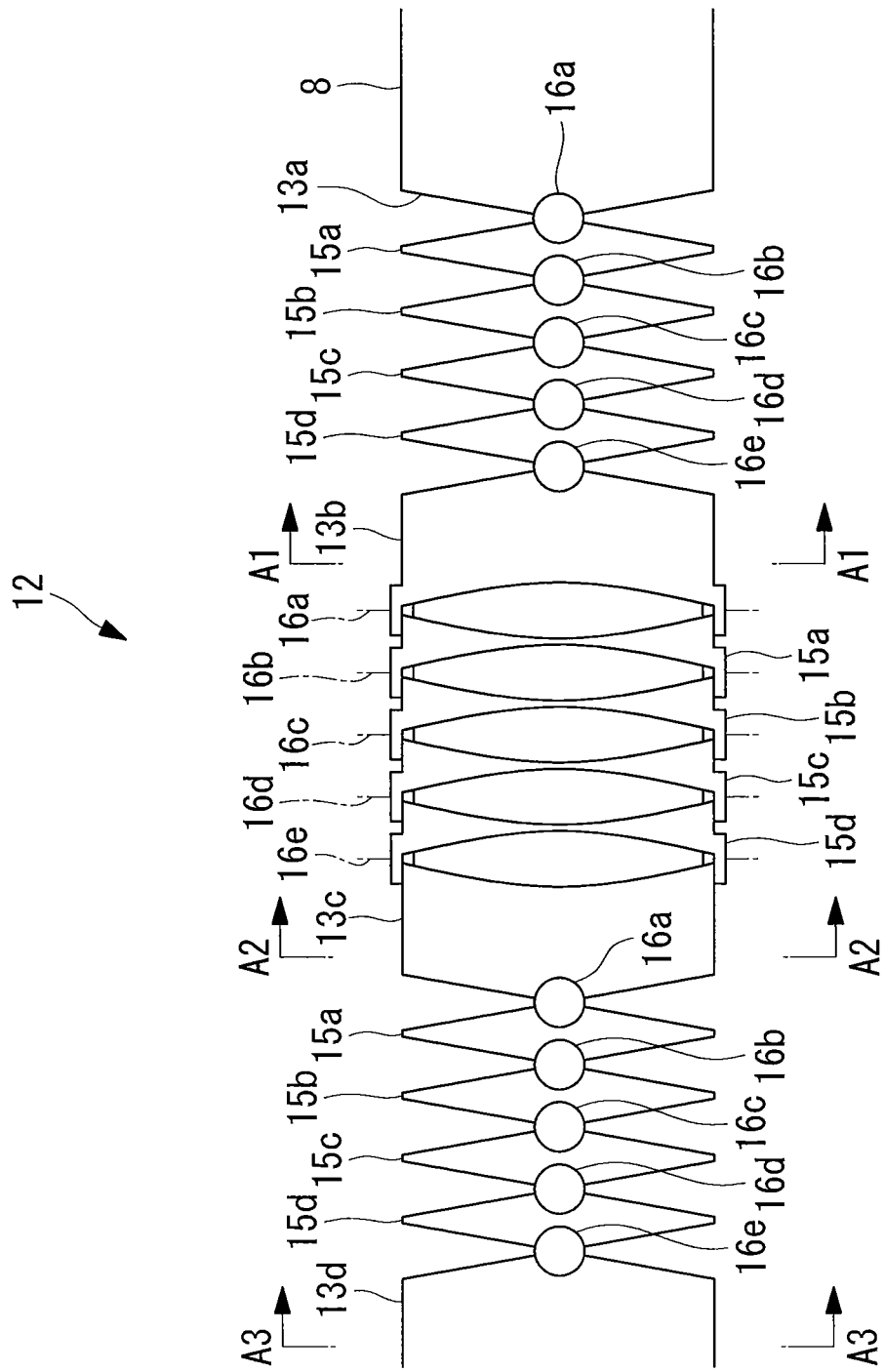
FIG. 13 is a side view illustrating a basal-end joint group in which flexure joints with different flexing directions are alternately arranged.
Figure 14A:
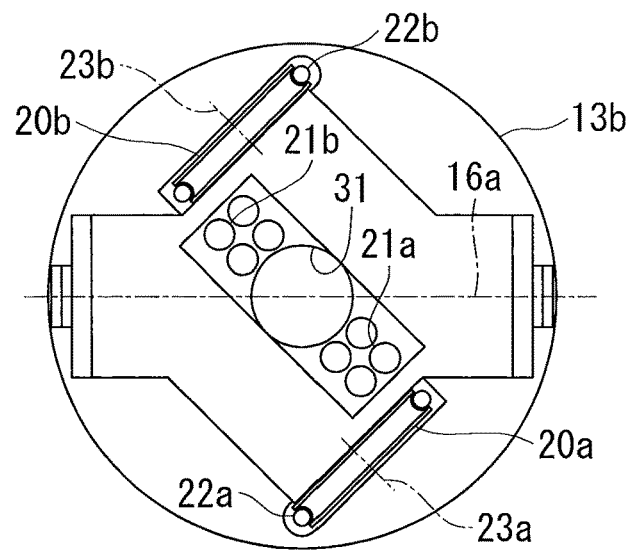
FIG. 14A is a front view showing the link member located closest to the basal end in FIG. 13.
Figure 14B:
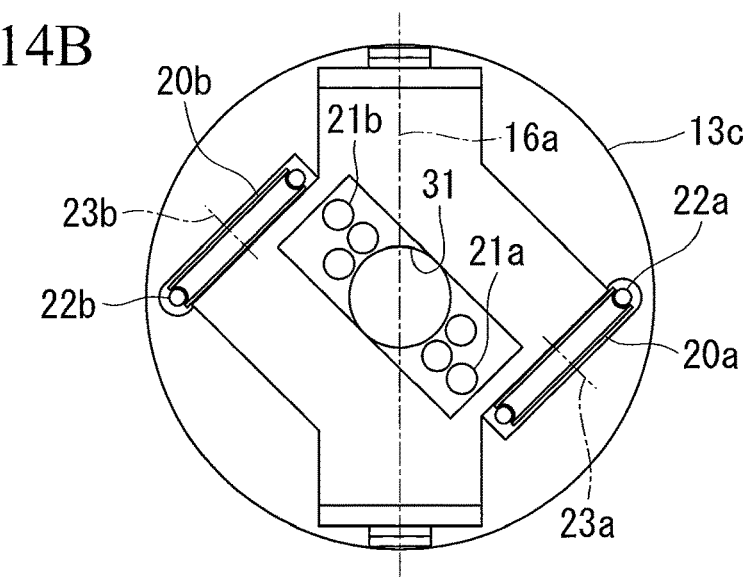
FIG. 14B is a front view showing the second link member from the basal end in FIG. 13.
Figure 14C:
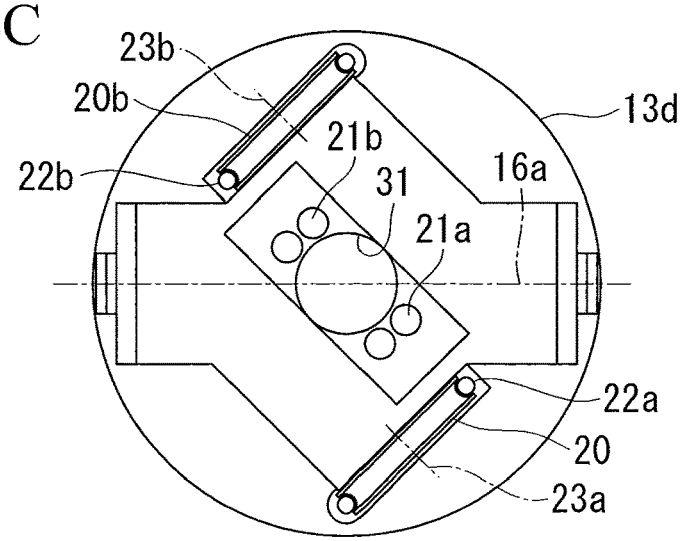
FIG. 14C is a front view showing the third link member from the basal end in FIG. 13.
Figure 15A:
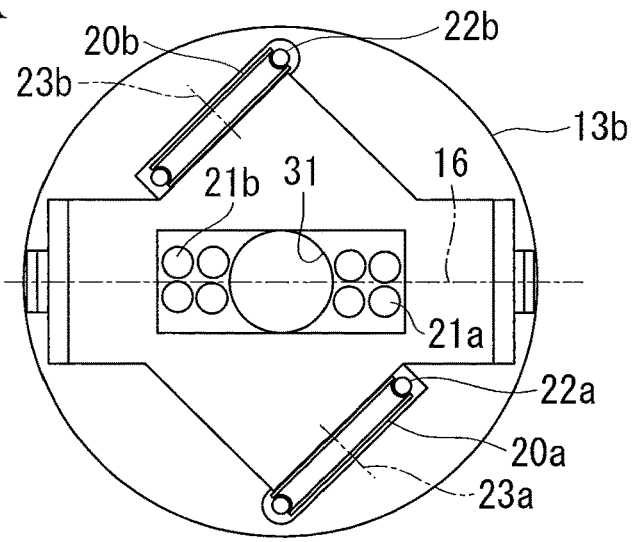
FIG. 15A illustrates a modification of FIG. 14A and is a front view showing the link member located closest to the basal end.
Figure 15B:
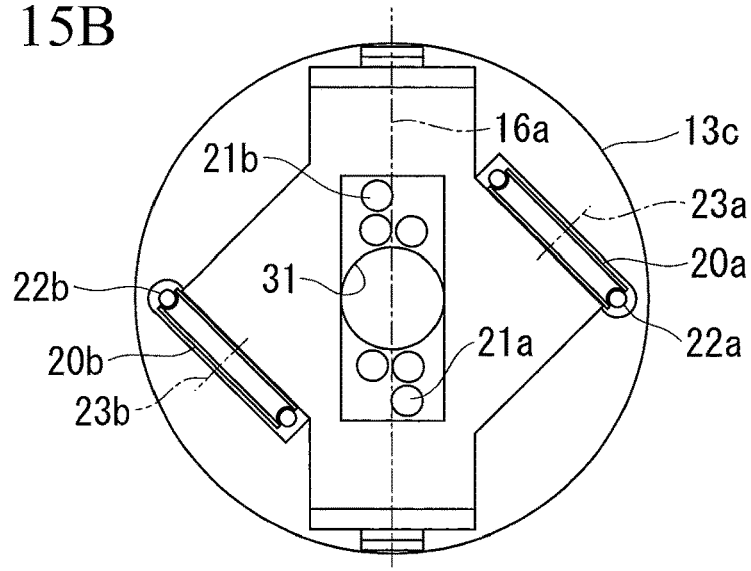
FIG. 15B illustrates a modification of FIG. 14B and is a front view showing the second link member from the basal end.
Figure 15C:
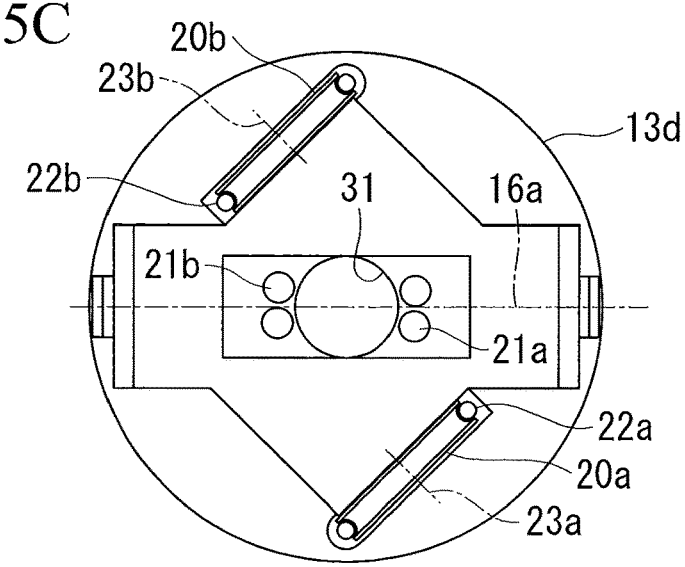
FIG. 15C illustrates a modification of FIG. 14C and is a front view showing the third link member from the basal end.

Furthermore, in this embodiment, the basal-end joint group 12 is constituted of four flexure joints 12a to 12d having substantially parallel axes 14a to 14d. Alternatively, as shown in FIG. 13, a basal-end joint group 12 in which the flexing direction alternately changes in orthogonal directions may be employed. In this case, as shown in FIGS. 14A, 14B, and 14C, the positions of the guide sheaths 21a and 21b may be identical among the link members 13b to 13e, and the link members 13b to 13e with the pulleys 20a and 20b disposed at different positions may be alternately disposed. As another alternative, as shown in FIGS. 15A, 15B, and 15C, the phases of the identical link members 13b to 13e may be varied by 90°. Reference sign 31 denotes a channel through which, for example, wires with higher rigidity than the guide sheaths 21a and 21b extend.

Furthermore, in this embodiment, the endoscope 5 having the basal-end joint group 12 with the four series-connected flexure joints 12a to 12d is described as an example. Alternatively, as shown in FIG. 16, the embodiment may be applied to a manipulator 5 having a single flexure joint 12a.

Figure 17:
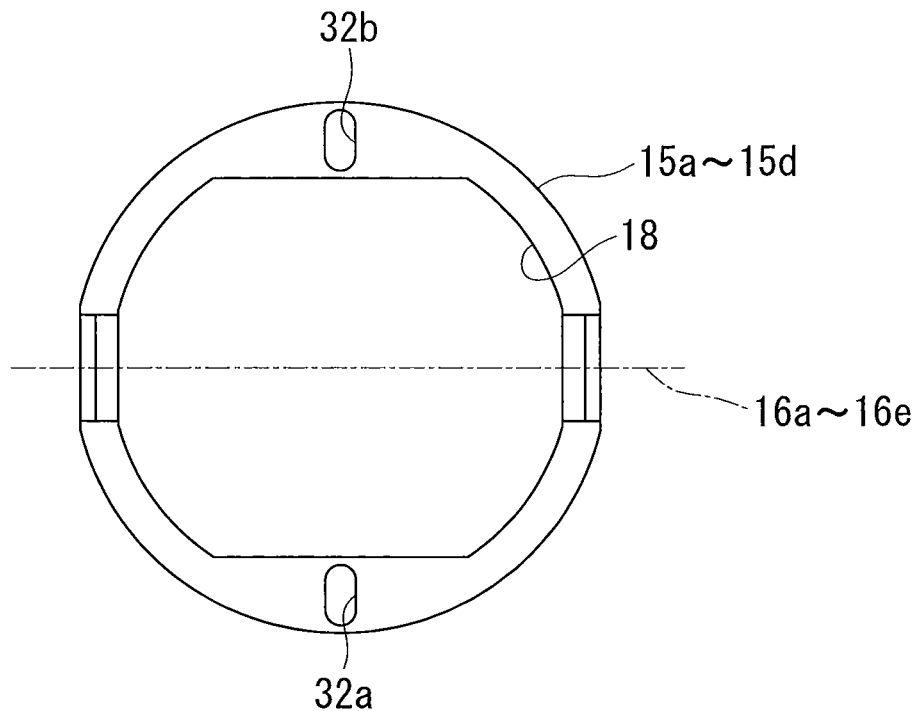
FIG. 17 is a front view illustrating a modification of segments.
Figure 18:
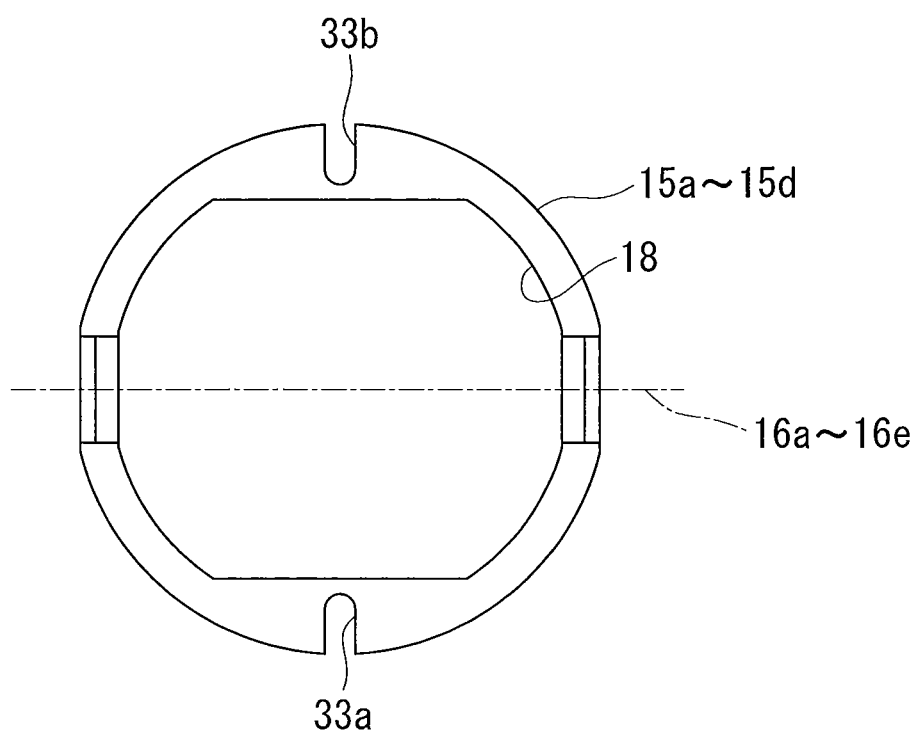
FIG. 18 is a front view illustrating another modification of the segments.

Furthermore, the segments 15a to 15d are described as having the through-holes 24a and 24b through which the manipulation wires 22a and 22b extend. Alternatively, as shown in FIGS. 17 and 18, the pass-through sections through which the manipulation wires 22a and 22b extend may have long holes 32a and 32b or grooves 33a and 33b extending in a direction orthogonal to the axes 16a to 16e.

As shown in FIG. 16, in a case where the through-holes 24a and 24b have an inside diameter that is slightly larger than the outside diameter of the manipulation wires 22a and 22b, the segments 15a to 15d swivel when the flexure joints 12a to 12d are flexed, causing the through-holes 24a and 24b provided in the segments 15a to 15d to be arranged along curved lines. Thus, each manipulation wire 22a or 22b extending through the through-holes 24a or 24b is bent so as to connect the through-holes 24a or 24b.

Figure 19:
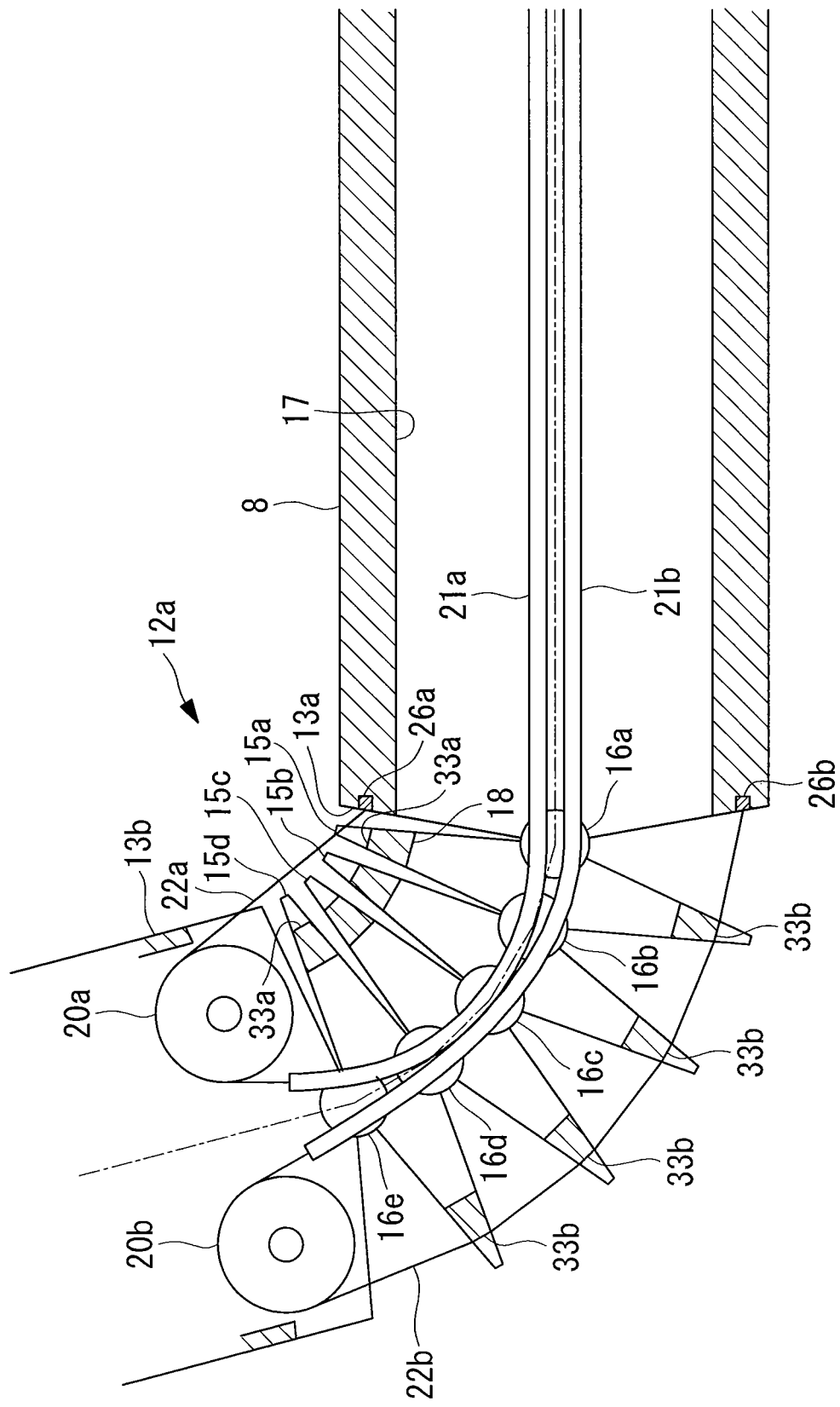
FIG. 19 is a vertical sectional view illustrating a bendable section having the segments in FIG. 18.

In this case, since the tension generated in the manipulation wires 22a and 22b increases in accordance with the magnitude of the traction force F, the manipulation wires 22a and 22b become pressed against the inner surfaces of the through-holes 24a and 24b, thus resulting in increased friction. In contrast, as shown in FIGS. 17 and 18, by forming the pass-through sections as long holes 32a and 32b or grooves 33a and 33b, deformation of the manipulation wires 22a and 22b in the radial direction is reduced when the flexure joints 12a to 12d are flexed, as shown in FIG. 19, so that the frictional force between the manipulation wires 22a and 22b and the inner surfaces of the long holes 32a and 32b or the grooves 33a and 33b is reduced even when the tension increases, thereby ensuring smooth movement of the manipulation wires 22a and 22b. FIG. 19 illustrates a flexed state in a case where the pass-through sections are the grooves 33a and 33b.

Although the endoscope 5 and the endoscope system 1 are described as examples of a manipulator and a manipulator system in this embodiment, the embodiment may alternatively be applied to other types of manipulators and manipulator systems, such as a surgical device.

Furthermore, although flexure joints provided in the endoscope 5 in the slave device 3 are described as an example, the embodiment may alternatively be applied to flexure joints provided in a manual endoscope.

Furthermore, examples of the manipulation wires 22a and 22b include solid wires, stranded wires, braided wires, and plates.

Consequently, the above-described embodiment derives the following solutions.

A first aspect of the present invention provides a joint mechanism including a tubular first member having a through-hole extending along a central axis; a second member disposed at a distal end of the first member and swivelable relative to the first member about a swivel axis intersecting the central axis; a flexible, tubular guide sheath extending near the central axis of the through-hole in the first member and a distal end of which is fixed to the second member; a manipulation wire introduced toward the distal end of the guide sheath via the guide sheath; and a turnaround section that is provided in the second member at a position decentered from the swivel axis in a radial direction and that causes the manipulation wire introduced from the first member via the guide sheath to make a U-turn toward the first member. A distal end of the manipulation wire caused to make a U-turn at the turnaround section is fixed to the first member at a position decentered from the swivel axis in the radial direction.

According to this aspect, when a traction force acting toward the basal end is applied to the basal end of the manipulation wire, the traction force propagates through the manipulation wire to the distal end thereof so as to act in a direction in which the turnaround section that causes the manipulation wire to make a U-turn and the first member to which the distal end of the manipulation wire is fixed are brought closer to each other. Since the positions where the turnaround section and the manipulation wire are fixed to the first member are decentered from the swivel axis in the radial direction, moment according to the decentered amount and the magnitude of the traction force is generated, so that the second member can be made to swivel relative to the first member in one direction about the swivel axis.

In this case, when the second member swivels relative to the first member, the guide sheath whose distal end is fixed to the second member also bends in the swiveling direction of the second member. However, since the guide sheath extends near the central axis of the joint mechanism and the manipulation wire alone is disposed near the outer periphery of the joint mechanism, the guide sheath, which has relatively high rigidity, can be prevented from being bent with an extremely small radius of curvature, thereby allowing for bending with a small traction force. As a result, reduced device size and improved controllability can be achieved.

In the above aspect, the turnaround section may be a pulley around which the manipulation wire is wound to cause the manipulation wire to make a U-turn.

Accordingly, when causing the second member to swivel relative to the first member by applying a traction force to the manipulation wire, the pulley is rotated so that the manipulation wire can be moved with a small frictional force, thereby allowing for bending with an even smaller traction force.

Furthermore, in the above aspect, the turnaround section may be a substantially U-shaped tubular member that allows the manipulation wire to extend therethrough so as to cause the manipulation wire to make a U-turn.

Accordingly, when causing the second member to swivel relative to the first member by applying a traction force to the manipulation wire, the manipulation wire can be moved within the tubular member while a fixed radius of curvature is maintained by the tubular member, thereby allowing for bending with a stable traction force.

Furthermore, in the above aspect, the guide sheath, the manipulation wire, and the turnaround section may include a pair of guide sheaths, a pair of manipulation wires, and a pair of turnaround sections, respectively, so as to cause the second member to swivel relative to the first member in two directions about the swivel axis.

Accordingly, the second member can be made to swivel relative to the first member in one direction by applying a traction force to one of the manipulation wires, and the second member can be made to swivel relative to the first member in the other direction by applying a traction force to the other manipulation wire. In the case where the second member is made to swivel relative to the first member in two directions about the swivel axis in this manner, the advantage of making the guide sheath extend near the central axis is high particularly in that the guide sheath can be prevented from being bent with an extremely small radius of curvature for both of the two directions.

Furthermore, in the above aspect, the pair of turnaround sections may be provided to cause the pair of manipulation wires to make a U-turn at positions partially overlapping each other in the radial direction.

Accordingly, the diameter of the turnaround sections can be made larger than the radius of the second member so that when the manipulation wires are caused to make a U-turn, a frictional force occurring between the manipulation wires and the turnaround sections can be reduced.

Furthermore, in the above aspect, the joint mechanism may further include one or more intermediate members provided between the first member and the second member and connected in a swivelable manner about two or more intermediate axes that are parallel to each other.

Accordingly, by causing the intermediate members to swivel about the intermediate axes, the positions of the intermediate axes are moved in the swiveling direction, so that a large overall swivel-angle range of the second member relative to the first member can be ensured.

Furthermore, in the above aspect, each intermediate member may be provided with a sheath pass-through hole that allows the guide sheath to extend therethrough and a wire pass-through section that allows the manipulation wire to extend therethrough. Moreover, the wire pass-through section may be a long hole or a cutout extending in a direction orthogonal to the intermediate axes.

Accordingly, the manipulation wire is moved through the wire pass-through section defined by a long hole or a cutout in the direction orthogonal to the intermediate axes in accordance with the swivel angle of the second member relative to the first member, so that a force applied to the manipulation wire in the lateral direction can be released as much as possible, whereby friction occurring when the manipulation wire moves can be reduced. Consequently, the second member can be made to swivel relative to the first member by simply applying a small traction force to the manipulation wire.

A second aspect of the present invention provides a manipulator including two or more series-connected joint mechanisms described above.

According to this aspect, an even larger overall bending-angle range can be ensured.

In the above aspect, the turnaround sections provided in the respective joint mechanisms may be disposed at substantially identical positions in the radial direction and a circumferential direction of the second members.

Accordingly, the plurality of first members, the plurality of second members, and the plurality of turnaround sections can respectively have identical shapes, thereby achieving commonality of components. Moreover, the turnaround sections and the distal ends of the manipulation wires, to which a traction force is to be applied, are fixed at identical positions so that uniform controllability can be achieved for all of the joint mechanisms.

Furthermore, in the above aspect, the turnaround sections provided in the respective joint mechanisms may be disposed at substantially identical positions in the radial direction of the second members but at different positions in a circumferential direction.

Accordingly, the routing of the manipulation wires from the openings at the distal ends of the guide sheaths toward the turnaround sections can be performed without difficulty while maintaining substantially identical fixation positions for the turnaround sections and the distal ends of the manipulation wires, to which a traction force is to be applied.

A third aspect of the present invention provides a manipulator including a tubular manipulator body, a basal-end joint unit provided at a distal end of the manipulator body, and a distal-end joint unit connected in series to a distal end of the basal-end joint unit and equipped with at least one joint mechanism described above. The basal-end joint unit includes a swivel member connected to the manipulator body in a swivelable manner about a swivel axis, a tubular guide sheath whose opening at a distal end thereof is fixed to the manipulator body, and a manipulation wire that is introduced via the guide sheath and protrudes from the opening at the distal end of the guide sheath and a distal end of which is fixed to a position decentered from the swivel axis of the swivel member in a radial direction.

According to this aspect, in the basal-end joint unit located closest to the manipulator body, the swivel member can be made to swivel relative to the manipulator body by pulling the swivel member from the manipulator body side toward the basal end. Consequently, the number of guide sheaths extending through the basal-end joint unit can be reduced so that the rigidity can be reduced, whereby the basal-end joint unit can be bent with a small traction force.

A fourth aspect of the present invention provides a manipulator including a tubular manipulator body having a through-hole extending along a central axis; a swivel member disposed at a distal end of the manipulator body and swivelable relative to the manipulator body about a swivel axis intersecting the central axis; a flexible, tubular guide sheath extending near the central axis of the through-hole in the manipulator body and a distal end of which is fixed to the swivel member; a manipulation wire introduced toward the distal end of the guide sheath via the guide sheath; and a turnaround section that is provided in the swivel member and that causes the manipulation wire introduced from the manipulator body via the guide sheath to make a U-turn toward the manipulator body. A distal end of the manipulation wire caused to make a U-turn at the turnaround section is fixed to the manipulator body at a position decentered from the swivel axis in the radial direction.

According to this aspect, even in a manipulator having a single joint mechanism disposed at the distal end of the manipulator body, a traction force can be applied to a position sufficiently decentered from the swivel axis in the radial direction by causing the manipulation wire to make a U-turn and fixing the distal end thereof to the manipulator body, whereby the swivel member can be made to swivel with a small traction force.

A fifth aspect of the present invention provides a manipulator system including the above-described manipulator, a slave device equipped with a driver that drives the manipulator, a master device equipped with an operation section to be operated by an operator, and a controller that controls the driver of the slave device based on an input signal input via the operation section of the master device.

Advantageous Effects of Invention

The present invention is advantageous in that it achieves bendability with a small traction force, reduced device size, and improved controllability.

REFERENCE SIGNS LIST

A surgeon (operator)
1 endoscope system (manipulator system)
2 master device
3 slave device
4 controller
5 endoscope (manipulator)
8 flexible section (manipulator body)
12a to 12d flexure joints (joint mechanism)
13a link member (first member)
13b link member (second member)
14a swivel axis
15a to 15d intermediate members
16a to 16e intermediate axes
17 through-hole
18 through-hole (sheath pass-through hole)
20a, 20b pulleys (turnaround sections)
21a, 21b guide sheaths
22a, 22b manipulation wires
24a through-hole (wire pass-through sections)
30a, 30b tubular members (turnaround sections)
32a, 32b long holes (wire pass-through sections)
33a, 33b grooves (wire pass-through sections)

What is claimed is:

1. A manipulator comprising:
    two or more series-connected joint mechanisms, wherein the two or more series-connected joint mechanisms each comprise:
    a tubular first member having an inner surface defining a through-hole extending along a first central axis;
    a second member disposed at a distal end of the first member and having a second central axis, the second member being swivelable relative to the first member about a swivel axis intersecting the second central axis;
    a flexible, tubular guide sheath extending near the central axes of the first and second members, a distal end of the flexible tubular guide sheath being directly fixed to the second member;
    a manipulation wire introduced toward the distal end of the guide sheath via the guide sheath; and
    at least one pulley provided in the second member such that the manipulation wire introduced from the first member via the guide sheath is wound at least partially around the at least one pulley to cause a distal end of the manipulation wire to change direction towards the first member, the at least one pulley being rotatable about a rotation axis;
    wherein the distal end of the manipulation wire is fixed to the first member.

2. The manipulator according to claim 1, wherein
    the at least one pulley comprises first and second pulleys; and
    the first and second pulleys are provided symmetrically with respect to the swivel axis of the second member.

3. The manipulator according to claim 2, wherein the first and second pulleys are provided on a same plane perpendicular to the swivel axis.

4. The manipulator according to claim 2, wherein the first and second pulleys are provided on different planes, each different plane being perpendicular to the swivel axis.

5. The manipulator according to claim 2, wherein the first and second pulleys are wholly disposed on separate sides of the swivel axis.

6. The manipulator according to claim 2, wherein the first and second pulleys are disposed such that a portion of the first and second pulleys overlap the swivel axis.

7. The manipulator according to claim 1, wherein the guide sheath, the manipulation wire, and the at least one pulley comprise a pair of guide sheaths, a pair of manipulation wires, and a pair of pulleys, respectively, so as to cause the second member to swivel relative to the first member in two directions about the swivel axis.

8. The manipulator according to claim 1, further comprising one or more intermediate members provided between the first member and the second member and connected in a swivelable manner about two or more intermediate axes that are parallel to each other.

9. The manipulator according to claim 1, wherein the distal end of the manipulation wire is fixed to the inner surface of the first member.

10. A manipulator comprising:
two or more series-connected joint mechanisms, wherein the two or more series-connected joint mechanisms each comprise:
a tubular first member having an inner surface defining a through-hole extending along a first central axis;
a second member disposed at a distal end of the first member and having a second central axis, the second member being swivelable relative to the first member about a swivel axis intersecting the second central axis;
a flexible, tubular guide sheath extending along the central axes of the first and second members, a distal end of the flexible tubular guide sheath being fixed to the second member;
a manipulation wire introduced toward the distal end of the guide sheath via the guide sheath; and
a first pulley and a second pulley provided in the second member such that the manipulation wire introduced from the first member via the guide sheath is wound at least partially around the at least one pulley to cause a distal end of the manipulation wire to change direction towards the first member, the first pulley and the second pulley being rotatable about a rotation axis, the first pulley and the second pulley provided symmetrically with respect to the swivel axis of the second member;
wherein the distal end of the manipulation wire is fixed to the first member; and
wherein the first pulley and the second pulley are provided on different planes, each different plane being perpendicular to the swivel axis.

11. The manipulator according to claim 10, wherein the guide sheath, the manipulation wire, and the the first pulley and the second pulley comprise a pair of guide sheaths, a pair of manipulation wires, and a pair of pulleys, respectively, so as to cause the second member to swivel relative to the first member in two directions about the swivel axis.

12. The manipulator according to claim 10, further comprising one or more intermediate members provided between the first member and the second member and connected in a swivelable manner about two or more intermediate axes that are parallel to each other.

13. The manipulator according to claim 10, wherein the distal end of the manipulation wire is fixed to the inner surface of the first member.

14. A manipulator comprising:
two or more series-connected joint mechanisms, wherein the two or more series-connected joint mechanisms each comprise:
a tubular first member having an inner surface defining a through-hole extending along a first central axis;
a second member disposed at a distal end of the first member and having a second central axis, the second member being swivelable relative to the first member about a swivel axis intersecting the second central axis;
a flexible, tubular guide sheath extending along the central axes of the first and second members, a distal end of the flexible tubular guide sheath being fixed to the second member;
a manipulation wire introduced toward the distal end of the guide sheath via the guide sheath; and
a first pulley and a second pulley provided in the second member such that the manipulation wire introduced from the first member via the guide sheath is wound at least partially around the at least one pulley to cause a distal end of the manipulation wire to change direction towards the first member, the first pulley and the second pulley being rotatable about a rotation axis, the first pulley and the second pulley provided symmetrically with respect to the swivel axis of the second member;
wherein the distal end of the manipulation wire is fixed to the first member
wherein the first pulley and the second pulley are disposed such that a portion of the first pulley and the second pulley overlap the swivel axis.

15. The manipulator according to claim 14, wherein the guide sheath, the manipulation wire, and the the first pulley and the second pulley comprise a pair of guide sheaths, a pair of manipulation wires, and a pair of pulleys, respectively, so as to cause the second member to swivel relative to the first member in two directions about the swivel axis.

16. The manipulator according to claim 14, further comprising one or more intermediate members provided between the first member and the second member and connected in a swivelable manner about two or more intermediate axes that are parallel to each other.

17. The manipulator according to claim 14, wherein the distal end of the manipulation wire is fixed to the inner surface of the first member.

* * * * *